(12) United States Patent
Pfister et al.

(10) Patent No.: US 8,742,131 B2
(45) Date of Patent: *Jun. 3, 2014

(54) 7-AZONIABICYCLO [2.2.1] HEPTANE DERIVATIVES, METHODS OF PRODUCTION, AND PHARMACEUTICAL USES THEREOF

(75) Inventors: Jürg R. Pfister, Sunnyvale, CA (US); Gwenaella Rescourio, Sunnyvale, CA (US); Meenakshi S. Venkatraman, Sunnyvale, CA (US); Xiaoming Zhang, Sunnyvale, CA (US)

(73) Assignee: Theron Pharmaceuticals, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/512,873

(22) PCT Filed: Jan. 27, 2011

(86) PCT No.: PCT/US2011/022760
§ 371 (c)(1), (2), (4) Date: Oct. 16, 2012

(87) PCT Pub. No.: WO2011/094434
PCT Pub. Date: Aug. 4, 2011

(65) Prior Publication Data
US 2013/0059898 A1    Mar. 7, 2013

Related U.S. Application Data

(60) Provisional application No. 61/386,450, filed on Sep. 24, 2010, provisional application No. 61/336,952, filed on Jan. 28, 2010.

(51) Int. Cl.
*C07D 487/08* (2006.01)
*C07D 487/10* (2006.01)
*A61K 31/403* (2006.01)

(52) U.S. Cl.
USPC ............ 548/411; 548/453; 514/409; 514/413

(58) Field of Classification Search
None
See application file for complete search history.

(56) References Cited

U.S. PATENT DOCUMENTS

| 4,353,922 A | 10/1982 | Pfister |
| 6,307,060 B1 | 10/2001 | Noe et al. |
| 2012/0029044 A1 | 2/2012 | Pfister et al. |

FOREIGN PATENT DOCUMENTS

WO    WO 2011/094434 A2    8/2011

OTHER PUBLICATIONS

Aaron, et al. Azabicyclic alcohols. IV. Stereochemistry of the 1- and 2-hydroxyindolizidine and ydroxypyrrolizidine systems. J Org. Chem. Nov. 1966; 31:3502-3507.
Abdel-Magid, et al.Reductive Amination of Aldehydes and Ketones with Sodium Triacetoxyborohydride. Studies on Direct and Indirect Reductive Amination Procedures(1). J Org Chem. May 31, 1996;61(11):3849-3862.
Berge, et al. Pharmaceutical salts. J Pharm Sci. Jan. 1977;66(1):1-19.
Bighley, et al. Salt Forms of Drugs and Absorption. in Swarbrick J, Boylan JC, eds. Encyclopedia of Pharmaceutical Technology 13, New York, NY: Marcel Dekker; 1996:453-499.
Boireau, et al. Addition diastereoselective d'organozinciques sur le phenylglyoxalate de (−) menthyle. Tetrahedron Letters. 1988; 29(18):2175-2176. (with English abstract).
Caulfield. Muscarinic receptors—characterization, coupling and function. Pharmacol Ther. Jun. 1993;58(3):319-79.
Fletcher, et al. Total Synthesis and Determination of the Absolute Configuration of Epibatidine. J. Org. Chem. 1994; 59:1771-1778.
Fryer, et al. Effects of inflammatory cells on neuronal M2 muscarinic receptor function in the lung. Life Sci. 1999;64(6-7):449-55.
Fryer, et al. Muscarinic receptors and control of airway smooth muscle. Am J Respir Crit Care Med. Nov. 1998;158(5 Pt 3):S154-60.
Hickey, Anthony J., ed., Pharmaceutical Inhalation Aerosol Technology, 2nd Ed., New York: Marcel Dekker, 2004.
Langer, et al. Erodible Systems. in "Treatise on Controlled Drug Delivery", A. Kydonieus Ed., Marcel Dekker, Inc., New York 1992; 199-224.
Lee, et al. Diffusion-Controlled Matrix Systems. in "Treatise on Controlled Drug Delivery", A. Kydonieus Ed., Marcel Dekker, Inc., New York 1992; 155-198.
Paulekuhn, et al. Trends in active pharmaceutical ingredient salt selection based on analysis of the Orange Book database. J Med Chem. Dec. 27, 2007;50(26):6665-72, Epub Dec. 1, 2007.
Pauwels, et al. Global strategy for the diagnosis, management, and prevention of chronic obstructive pulmonary disease. NHLBI/WHO Global Initiative for Chronic Obstructive Lung Disease (GOLD) Workshop summary. Am J Respir Crit Care Med. Apr. 2001;163(5):1256-76.
Peralta, et al. Distinct primary structures, ligand-binding properties and tissue-specific expression of four human muscarinic acetylcholine receptors. EMBO J. Dec. 20, 1987;6(13):3923-9.
Peralta, et al. Primary structure and biochemical properties of an M2 muscarinic receptor. Science. May 1, 1987;236(4801):600-5.
Pfister, et al. Synthesis and bronchodilator activity of endo-2-(2-cyclopentyl-2-hydroxy-2-phenyl)acetoxy-7-methyl-7-azabicyclo-[2.2.1]heptane methobromide, a potent and long-acting anticholinergic agent. J Pharm Sci. Feb. 1985;74(2):208-10.
Poste, et al. Lipid vesicles are carriers for introducing biologically active materials into cells. Prescott, Ed., Methods in Cell Biology, vol. XIV, Academic Press, New York, N.W. 1976; 33-71.
Ramanaiah, et al. Synthesis and stereochemical assignment of exo- and endo-7-methyl-7-azabicyclo[2.2.1]heptan-2-ol. Org Lett. Nov. 4, 1999;1(9):1439-41.
Remington: The Science and Practice of Pharmacy, Lippincott Williams & Wilkins, Philadelphia, 20th edition (2003).
Remington's Pharmaceutical Sciences, Mack Pub. Co., New Jersey (1991).
Office action dated May 8, 2013 for U.S. Appl. No. 13/722,957.
Barnes. Distribution of receptor targets in the lung. Proc Am Thorac Soc. 2004;1(4):345-51.
Barnes. Emerging pharmacotherapies for COPD. Chest. Dec. 2008;134(6):1278-86.
Casarosa, et al. Preclinical evaluation of long-acting muscarinic antagonists: comparison of tiotropium and investigational drugs. J Pharmacol Exp Ther. Aug. 2009;330(2):660-8. Epub May 28, 2009.
U.S. Appl. No. 13/722,957, filed Dec. 20, 2012, Pfister et al.
International preliminary report on patentability dated Nov. 15, 2012 for PCT Application No. US2011/22760.
Office action dated Jun. 27, 2012 for U.S. Appl. No. 13/015,496.
Office action dated Nov. 5, 2013 for U.S. Appl. No. 13/722,957.

*Primary Examiner* — Nyeemah A Grazier
(74) *Attorney, Agent, or Firm* — Wilson Sonsini Goodrich & Rosati, PC

(57) ABSTRACT

Muscarinic acetylcholine receptor antagonists and methods of using them for the treatment of muscarinic acetyl-choline receptor-mediated diseases, such as pulmonary diseases, are provided.

14 Claims, 2 Drawing Sheets

7-AZONIABICYCLO [2.2.1] HEPTANE DERIVATIVES, METHODS OF PRODUCTION, AND PHARMACEUTICAL USES THEREOF

CROSS-REFERENCE TO RELATED APPLICATIONS

This patent application claims priority benefit of U.S. Provisional Patent Application No. 61/336,952 filed Jan. 28, 2010, and of U.S. Provisional Patent Application No. 61/386,450 filed Sep. 24, 2010. The entire contents of those patent applications are hereby incorporated by reference herein.

FIELD OF THE INVENTION

This invention relates to 7-azoniabicyclo[2.2.1]heptane derivatives, pharmaceutical compositions of the derivatives, and the use thereof in treating muscarinic acetylcholine receptor mediated diseases of the respiratory tract.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs where they mediate many vital functions. Muscarinic receptors can mediate both inhibitory and excitatory actions. For example, in smooth muscle located in the airways, $M_3$ mAChRs mediate contractile responses. For a review, see Caufield, Pharmac. Ther. 58, 319 (1993).

In the lung, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For a review of mAChR expression and function in the lungs, see Fryer and Jacoby, Am. J. Respir. Crit. Care Med. 158, 154 (1998).

Three subtypes of mAChRs have been identified as important in the lungs, $M_1$, $M_2$ and $M_3$ mAChRs. The $M_3$ mAChRs, located on airway smooth muscle, mediate muscle contraction. Stimulation of $M_3$ mAChRs activates the enzyme phospholipase C via binding of the stimulatory G protein Gq/11 (Gs), leading to liberation of phosphatidyl inositol-4,5-bisphosphate, resulting in phosphorylation of contractile proteins. $M_3$ mAChRs are also found on pulmonary submucosal glands. Stimulation of this population of $M_3$ mAChRs results in mucus secretion.

$M_2$ mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal $M_2$ mAChRs are located on postganglionic parasympathetic nerves. Under normal physiologic conditions, neuronal $M_2$ mAChRs provide tight control of acetylcholine release from parasympathetic nerves. Inhibitory $M_2$ mAChRs have also been demonstrated on sympathetic nerves in the lungs of some species. These receptors inhibit release of noradrenaline, thus decreasing sympathetic input to the lungs.

$M_1$ mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lung has been noted in a variety of different pathophysiological states. In particular, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation (Fryer et al., Life Sci. 64, 449 (1999)). This mAChR dysfunction results in airway hyperreactivity and hyperresponsiveness mediated by increased stimulation of $M_3$ mAChRs. Thus the identification of potent mAChR antagonists would be useful as therapeutics in these mAChR-mediated disease states.

COPD is an imprecise term that encompasses a variety of progressive health problems including chronic bronchitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five diseases as a world-wide health burden by the year 2020. Inhaled anticholinergic therapy is currently considered the "gold standard" as first line therapy for COPD (Pauwels et al., Am. J. Respir. Crit. Care Med. 163, 1256 (2001)).

Despite the large body of evidence supporting the use of anticholinergic therapy for the treatment of airway hyperreactive diseases such as COPD, relatively few anticholinergic compounds are available for use in the clinic for pulmonary indications. More specifically, in the United States, ipratropium (Atrovent; also as Combivent in combination with albuterol) and tiotropium (Spiriva) are currently the only inhaled anticholinergics marketed for the treatment of hyperreactive airway diseases. While the latter is a potent and long-acting anti-muscarinic agent, it is not available as a combination with other pharmacological agents such as albuterol. This appears to be due to the lack of sufficient chemical stability of tiotropium in the presence of certain additional agents.

Thus, there remains a need for novel anticholinergic agents, i.e., agents that inhibit the binding of acetylcholine to its receptors, which can be co-formulated with other pharmaceuticals and which can be administered conveniently, such as once a day, for the treatment of hyperreactive airway diseases such as asthma and COPD.

Since mAChRs are widely distributed throughout the body, the ability to apply anticholinergic agents locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would avoid unwanted side effects that may be seen with systemic anticholinergic exposure. However, other muscarinic acetylcholine receptor-mediated diseases respond to systemic administration. Thus, medications useful for respiratory disorders can be administered systemically when appropriate for treatment of the respiratory disorder, or when appropriate for treatment of a non-respiratory disorder.

SUMMARY OF THE INVENTION

This invention provides for compounds useful for treating, and methods of treating, a muscarinic acetylcholine receptor (mAChR) mediated disease, which method comprises administering an effective amount of a stereochemically pure compound of Formula (I) or Formula (II).

This invention also relates to compounds which inhibit the binding of acetylcholine to its receptors. This invention also relates to methods of inhibiting the binding of acetylcholine to its receptors in a subject in need thereof which comprises administering to aforementioned subject an effective amount of a stereochemically pure compound of Formula (I) or Formula (II).

The present invention also provides for the novel stereochemically pure compounds of Formula (I) or Formula (II), and pharmaceutical compositions comprising a stereochemically pure compound of Formula (I) or Formula (II), and a pharmaceutically acceptable excipient, carrier, or diluent.

In one embodiment, the invention provides compounds having the structures shown by Formula (I):

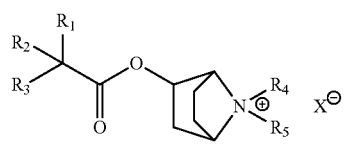

(I)

where $R_1$ is phenyl or thienyl, optionally substituted with alkyl, alkoxy, halo or COOR groups;

$R_2$ is $R_1$, cyclopentyl, cyclohexyl, 1-alkylcyclopentyl or 1-alkylcyclohexyl;

or $R_1$ and $R_2$ together can be 9-xanthenyl or 9-hydroxyxanthenyl optionally substituted on either or both benzene rings with alkyl, alkoxy, halo or COOR groups;

or the group $R_1R_2R_3C$ can be 10-phenothiazinyl optionally substituted on either or both benzene rings with alkyl, alkoxy, halo or COOR groups;

$R_3$ is H, or OH;

$R_4$ and $R_5$ are lower alkyl, alkoxycarbonylalkyl, aralkyl, or aryloxyalkyl (the latter two optionally substituted with alkyl, alkoxy, halo or the group COOR) or together form a five- or six-membered ring optionally substituted with aryl or aryloxy;

R is lower alkyl; and $X^-$ represents a pharmaceutically acceptable anion associated with the positive charge of the N atom, including but not limited to chloride, bromide, iodide, sulfate, methanesulfonate, benzenesulfonate, and toluenesulfonate. $X^-$ can be a monovalent or polyvalent anion.

In another embodiment, the invention provides a compound of Formula (I), wherein the compound is stereochemically pure.

In one embodiment, $R_1$ is independently selected from phenyl, optionally substituted with alkyl, alkoxy, halo or COOR groups, such as —$C_1$-$C_8$ alkyl, —O—$C_1$-$C_8$ alkyl, —F, —Cl, —Br, —I, or —C(=O)O—$C_1$-$C_4$ alkyl groups. In another embodiment, $R_1$ is unsubstituted phenyl.

In one embodiment, $R_2$ is cyclopentyl.

In one embodiment, $R_3$ is OH.

In one embodiment, $R_4$ and $R_5$ are independently selected from $C_1$-$C_4$ alkyl. In another embodiment, both $R_4$ and $R_5$ are methyl.

In one embodiment, the invention embraces an isolated compound of Formula (I), optionally additionally comprising a pharmaceutically acceptable carrier or excipient, and optionally additionally comprising one or more other therapeutic agents. In one embodiment, the invention embraces an isolated, stereochemically pure compound of Formula (I), optionally additionally comprising a pharmaceutically acceptable carrier or excipient, and optionally additionally comprising one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the invention provides a stereochemically pure compound of the structure shown by Formula (II):

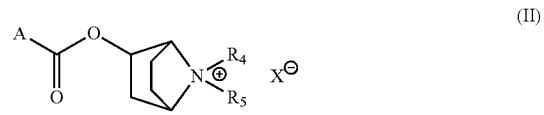

(II)

where A is independently selected from the group consisting of:

—C($R_1$)($R_2$)($R_3$), where $R_1$ is independently selected from phenyl or thienyl, optionally substituted with alkyl, alkoxy, halo or COOR groups, such as —$C_1$-$C_8$ alkyl, —O—$C_1$-$C_8$ alkyl, —F, —Cl, —Br, —I, or —C(=O)—O—$C_1$-$C_4$ alkyl groups;

where $R_2$ is independently selected from phenyl, thienyl, cyclopentyl, cyclohexyl, 1-hydroxycyclopentyl or 1-hydroxycyclohexyl, where phenyl, thienyl, cyclopentyl, cyclohexyl, 1-hydroxycyclopentyl or 1-hydroxycyclohexyl are optionally substituted with alkyl, alkoxy, halo or COOR groups, such as —$C_1$-$C_8$ alkyl, —O—$C_1$-$C_8$ alkyl, —F, —Cl, —Br, —I, or —C(=O)—O—$C_1$-$C_4$ alkyl groups; and where $R_3$ is H or OH;

9-xanthenyl or 9-hydroxyxanthenyl, optionally substituted on either or both benzene rings with alkyl, alkoxy, halo or COOR groups, such as —$C_1$-$C_8$ alkyl, —O—$C_1$-$C_8$ alkyl, —F, —Cl, —Br, —I, or —C(=O)—O—$C_1$-$C_4$ alkyl groups; and 10-phenothiazinyl, optionally substituted on either or both benzene rings with alkyl, alkoxy, halo or COOR groups, such as —$C_1$-$C_8$ alkyl, —O—$C_1$-$C_8$ alkyl, —F, —Cl, —Br, —I, or —C(=O)—O—$C_1$-$C_4$ alkyl groups;

$R_4$ and $R_5$ are independently selected from lower alkyl (such as $C_1$-$C_4$ alkyl), alkoxycarbonylalkyl (such as —$C_1$-$C_8$ alkyl-O—(C=O)—$C_1$-$C_8$ alkyl), aralkyl (such as —$C_1$-$C_8$ alkyl-$C_6$-$C_{10}$ aryl), or aryloxyalkyl (such as —$C_1$-$C_8$ alkyl-O—$C_6$-$C_{10}$ aryl), where alkoxycarbonylalkyl and aralkyl can be optionally substituted with alkyl, alkoxy, halo or the group COOR (such as —$C_1$-$C_8$ alkyl, —O—$C_1$-$C_8$ alkyl, —F, —Cl, —Br, —I, or —C(=O)—O—$C_1$-$C_4$ alkyl groups) or together form a five- or six-membered ring optionally substituted with aryl (such as —$C_6$-$C_{10}$ aryl) or aryloxy (such as —O—$C_6$-$C_{10}$ aryl);

R is lower alkyl; and $X^\ominus$ represents a pharmaceutically acceptable anion, including but not limited to chloride, bromide, iodide, sulfate, methanesulfonate, benzenesulfonate, and toluenesulfonate. $X^-$ can be a monovalent or polyvalent anion.

In one embodiment, A is the group —C(R$_1$)(R$_2$)(R$_3$). In another embodiment, R$_1$ is independently selected from phenyl, optionally substituted with alkyl, alkoxy, halo or COOR groups, such as —C$_1$-C$_8$ alkyl, —O—C$_1$-C$_8$ alkyl, —F, —Cl, —Br, —I, or —C(=O)—O—C$_1$-C$_4$ alkyl groups. In another embodiment, R$_1$ is unsubstituted phenyl.

In one embodiment, A is the group —C(R$_1$)(R$_2$)(R$_5$). In another embodiment, R$_2$ is cyclopentyl.

In one embodiment, A is the group —C(R$_1$)(R$_2$)(R$_3$). In another embodiment, R$_3$ is OH.

In one embodiment, R$_4$ and R$_5$ are independently selected from C$_1$-C$_4$ alkyl. In another embodiment, both R$_4$ and R$_5$ are methyl.

In one embodiment, the invention embraces an isolated compound of Formula (II), optionally additionally comprising a pharmaceutically acceptable carrier or excipient, and optionally additionally comprising one or more other therapeutic agents. In one embodiment, the invention embraces an isolated, stereochemically pure compound of Formula (II), optionally additionally comprising a pharmaceutically acceptable carrier or excipient, and optionally additionally comprising one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

Included in the scope of this invention is each active, stereochemically pure isomer of a compound of Formula (I) or Formula (II), including crystalline forms, amorphous forms, hydrates, or solvates. The invention includes each isolated, stereochemically pure compound of Formula (I) or Formula (II).

The invention also embraces a pharmaceutical formulation comprising a stereochemically pure compound of Formula (I) or Formula (II) and a pharmaceutically acceptable carrier or excipient, and optionally one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the pharmaceutically acceptable anion associated with any of the compounds disclosed herein is selected from the group consisting of acetate, besylate (benzenesulfonate), benzoate, bicarbonate, bitartrate, bromide, calcium edetate, camphorsulfonate (camsylate), carbonate, chloride, chlorotheophyllinate, citrate, edetate, ethanedisulfonate (edisylate), ethanesulfonate (esylate), fumarate, gluceptate (glucoheptonate), gluconate, glucuronate, glutamate, hexylresorcinate, hydroxynaphthoate, hippurate, iodide, isethionate, lactate, lactobionate, lauryl sulfate (estolate), malate, maleate, mandelate, mesylate, methanesulfonate, methylnitrate, methylsulfate, mucate, naphthoate, napsylate, nitrate, octadecanoate, oleate, oxalate, pamoate, pantothenate, phosphate, polygalacturonate, salicylate, stearate, succinate, sulfate, subsalicylate, tannate, tartrate, teoclate, toluene sulfonate (tosylate), and trifluoroacetate. The anion can be a monovalent anion or a polyvalent anion.

The invention also embraces a method of using the present compounds, such as a stereochemically pure compound of Formula (I) or Formula (II), for treating a variety of indications, including but not limited to diseases mediated by muscarinic acetylcholine receptors. The invention also embraces a method of using the present compounds, such as a stereochemically pure compound of Formula (I) or Formula (II), for treating respiratory tract disorders such as chronic obstructive pulmonary disorder (COPD, also called chronic obstructive lung disease), chronic bronchitis, asthma, chronic respiratory obstruction, pulmonary fibrosis, pulmonary emphysema, rhinorrhea, allergic rhinitis, occupational lung diseases including pneumoconiosis (such as black lung disease, silicosis and asbestosis), acute lung injury (ALI), and acute respiratory distress syndrome (ARDS). Other, non-respiratory medical conditions that can be treated with muscarinic receptor antagonists include, but are not limited to, genitourinary tract disorders, such as urinary urge incontinence, overactive bladder or detrusor hyperactivity and their symptoms; gastroesophageal reflux disease (GERD); gastrointestinal tract disorders, such as irritable bowel syndrome, diverticular disease, achalasia, gastrointestinal hypermotility disorders and diarrhea; and the like.

In another embodiment, the invention embraces a stereochemically pure compound of the formula:

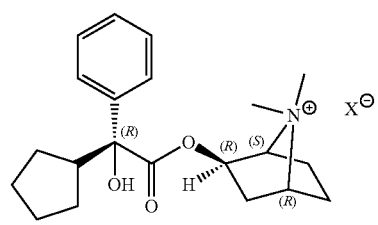

(1S,2R)-2-((R)-2'-cyclopentyl-2'-hydroxy 2'-phenylacetoxy)-7,7-dimethyl-7-azoniabicyclo[2.2.1]heptane with anion x$^\ominus$-;

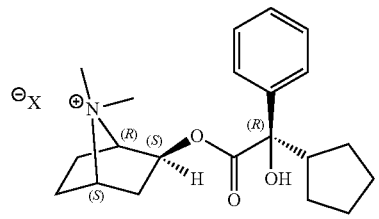

(1R,2S)-2-((R)-2'-cyclopentyl-2'-hydroxy 2'-phenylacetoxy)-7,7-dimethyl-7-azoniabicyclo[2.2.1]heptane with anion x$^\ominus$-;

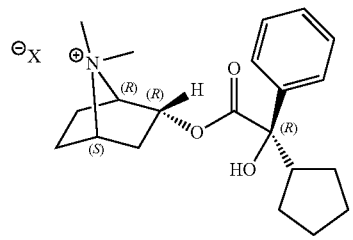

(1R,2R)-2-((R)-2'-cyclopentyl-2'-hydroxy 2'-phenylacetoxy)-7,7-dimethyl-7-azoniabicyclo[2.2.1]heptane with anion x$^\ominus$-; or

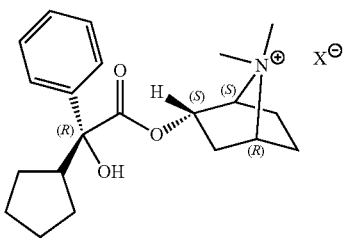

(1S,2S)-2-((R)-2'-cyclopentyl-2'-hydroxy 2'-phenylac-etoxy)-7,7-dimethyl-7-azoniabicyclo[2.2.1]heptane with anion x<sup>⊖</sup>;

where x<sup>⊖</sup> is a pharmaceutically acceptable anion. X<sup>−</sup> can be a monovalent anion or a polyvalent anion. Each compound can optionally additionally comprise a pharmaceutically acceptable carrier or excipient, and optionally additionally comprise one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In another embodiment, the invention embraces a stereochemically pure compound of the formula:

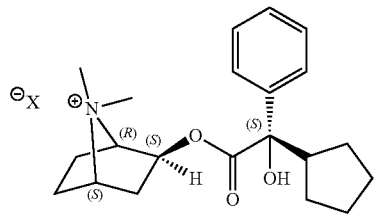

(1R,2S)-2-((S)-2'-cyclopentyl-2'-hydroxy 2'-phenylac-etoxy)-7,7-dimethyl-7-azoniabicyclo[2.2.1]heptane with anion x<sup>⊖</sup>;

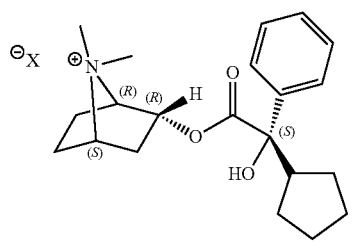

(1R,2R)-2-((S)-2'-cyclopentyl-2'-hydroxy 2'-phenylac-etoxy)-7,7-dimethyl-7-azoniabicyclo[2.2.1]heptane with anion x<sup>⊖</sup>;

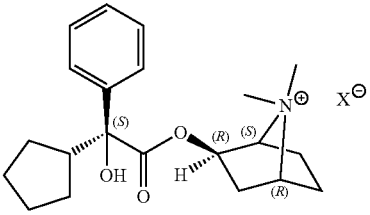

(1S,2S)-2-((S)-2'-cyclopentyl-2'-hydroxy 2'-phenylac-etoxy)-7,7-dimethyl-7-azoniabicyclo[2.2.1]heptane with anion x<sup>⊖</sup>; and

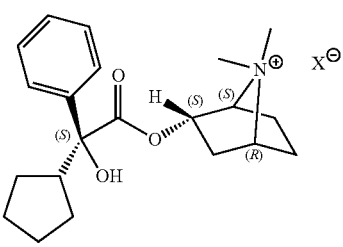

(1S,2S)-2-((S)-2'-cyclopentyl-2'-hydroxy 2'-phenylac-etoxy)-7,7-dimethyl-7-azoniabicyclo[2.2.1]heptane with anion x<sup>⊖</sup>;

where x<sup>⊖</sup> is a pharmaceutically acceptable anion. X<sup>−</sup> can be a monovalent anion or a polyvalent anion. Each compound can optionally additionally comprise a pharmaceutically acceptable carrier or excipient, and optionally additionally comprise one or more other therapeutic agents. The foregoing embodiments may optionally also add the proviso that the one or more other therapeutic agents exclude(s) compounds (1), (2), (3), and/or (4) as defined herein, or an alternate salt thereof. The foregoing embodiments may optionally also add the proviso that the one or more other therapeutic agents is not another compound of Formula (I) and/or Formula (II).

In another embodiment, the invention embraces specific compounds of the formula:

(1)

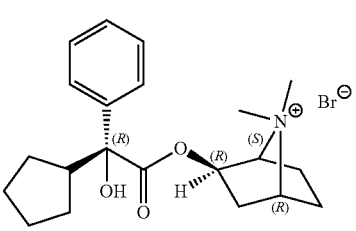

(1S,2R)-2-((R)-2'-cyclopentyl-2'-hydroxy 2'-phenylac-etoxy)-7,7-dimethyl-7-azoniabicyclo[2.2.1]heptane bromide;

(2)

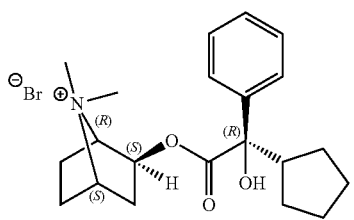

(1R,2S)-2-((R)-2'-cyclopentyl-2'-hydroxy 2'-phenylacetoxy)-7,7-dimethyl-7-azoniabicyclo[2.2.1]heptane bromide;

(3)

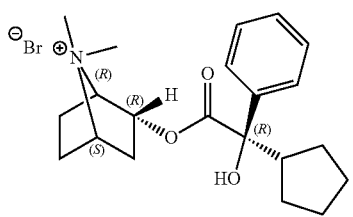

(1R,2R)-2-((R)-2'-cyclopentyl-2'-hydroxy 2'-phenylacetoxy)-7,7-dimethyl-7-azoniabicyclo[2.2.1]heptane bromide; and (4)

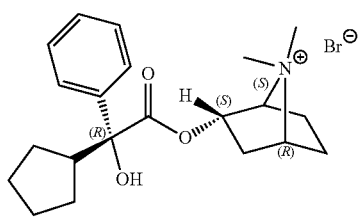

(1S,2S)-2-((R)-2'-cyclopentyl-2'-hydroxy 2'-phenylacetoxy)-7,7-dimethyl-7-azoniabicyclo[2.2.1]heptane bromide;

in stereochemically pure form. Each compound can optionally additionally comprise a pharmaceutically acceptable carrier or excipient, and optionally additionally comprise one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In another embodiment, the invention embraces specific compounds of the formula:

(5)

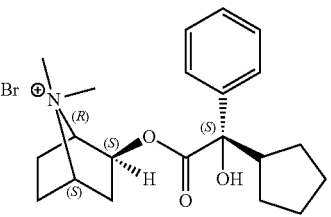

(1R,2S)-2-((S)-2'-cyclopentyl-2'-hydroxy 2'-phenylacetoxy)-7,7-dimethyl-7-azoniabicyclo[2.2.1]heptane bromide;

(6)

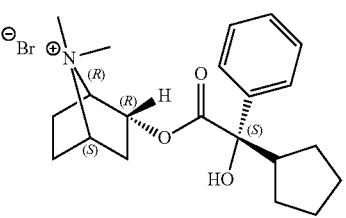

(1R,2R)-2-((S)-2'-cyclopentyl-2'-hydroxy 2'-phenylacetoxy)-7,7-dimethyl-7-azoniabicyclo[2.2.1]heptane bromide;

(7)

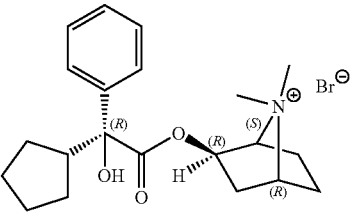

(1S,2R)-2-((S)-2'-cyclopentyl-2'-hydroxy 2'-phenylacetoxy)-7,7-dimethyl-7-azoniabicyclo[2.2.1]heptane bromide; and (8)

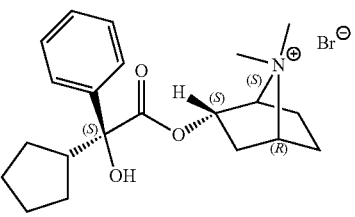

(1S,2S)-2-((S)-2'-cyclopentyl-2'-hydroxy 2'-phenylacetoxy)-7,7-dimethyl-7-azoniabicyclo[2.2.1]heptane bromide;

in stereochemically pure form. Each compound can optionally additionally comprise a pharmaceutically acceptable carrier or excipient, and optionally additionally comprise one or more other therapeutic agents. The foregoing embodiments may optionally also add the proviso that the one or more other therapeutic agents is not another compound of Formula (I) and/or Formula (II).

In another embodiment, the invention embraces a composition consisting essentially of a compound of the formula:

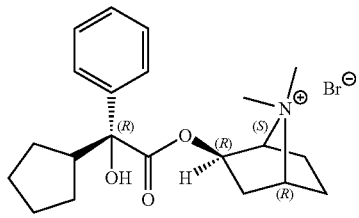

(1S,2R)-2-((R)-2'-cyclopentyl-2'-hydroxy 2'-phenylacetoxy)-7,7-dimethyl-7-azoniabicyclo[2.2.1]heptane bromide;

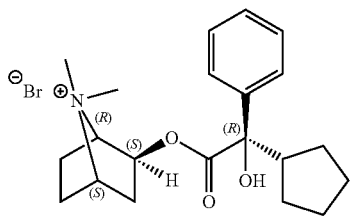

(1R,2S)-2-((R)-2'-cyclopentyl-2'-hydroxy 2'-phenylacetoxy)-7,7-dimethyl-7-azoniabicyclo[2.2.1]heptane bromide;

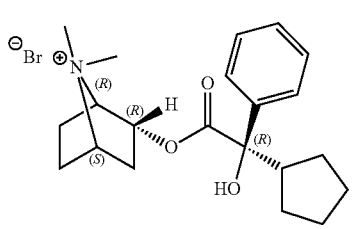

(1R,2R)-2-((R)-2'-cyclopentyl-2'-hydroxy 2'-phenylacetoxy)-7,7-dimethyl-7-azoniabicyclo[2.2.1]heptane bromide;

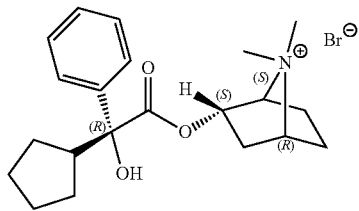

(1S,2S)-2-((R)-2'-cyclopentyl-2'-hydroxy 2'-phenylacetoxy)-7,7-dimethyl-7-azoniabicyclo[2.2.1]heptane bromide;
in stereochemically pure form, or consisting essentially of a mixture of (1), (2), (3), and (4) in any proportion, such as a 1:1:1:1 proportion. Each compound or mixture can optionally additionally consist essentially of one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the invention embraces an isolated compound of formula (1), optionally additionally comprising a pharmaceutically acceptable excipient or carrier, and optionally additionally comprising one or more other therapeutic agents. In one embodiment, the invention embraces a stereochemically pure compound of formula (1), optionally additionally comprising a pharmaceutically acceptable excipient or carrier, and optionally additionally comprising one or more other therapeutic agents. In one embodiment, the invention embraces an isolated, stereochemically pure compound of formula (1), optionally additionally comprising a pharmaceutically acceptable excipient or carrier, and optionally additionally comprising one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the invention embraces an isolated compound of formula (2), optionally additionally comprising a pharmaceutically acceptable excipient or carrier, and optionally additionally comprising one or more other therapeutic agents. In one embodiment, the invention embraces a stereochemically pure compound of formula (2), optionally additionally comprising a pharmaceutically acceptable excipient or carrier, and optionally additionally comprising one or more other therapeutic agents. In one embodiment, the invention embraces an isolated, stereochemically pure compound of formula (2), optionally additionally comprising a pharmaceutically acceptable excipient or carrier, and optionally additionally comprising one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the invention embraces an isolated compound of formula (3), optionally additionally comprising a pharmaceutically acceptable excipient or carrier, and optionally additionally comprising one or more other therapeutic agents. In one embodiment, the invention embraces a stereochemically pure compound of formula (3), optionally additionally comprising a pharmaceutically acceptable excipient or carrier, and optionally additionally comprising one or more other therapeutic agents. In one embodiment, the invention embraces an isolated, stereochemically pure compound of formula (3), optionally additionally comprising a pharmaceutically acceptable excipient or carrier, and optionally additionally comprising one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the invention embraces an isolated compound of formula (4), optionally additionally comprising a pharmaceutically acceptable excipient or carrier, and optionally additionally comprising one or more other therapeutic agents. In one embodiment, the invention embraces a stereochemically pure compound of formula (4), optionally additionally comprising a pharmaceutically acceptable excipient or carrier, and optionally additionally comprising one or more other therapeutic agents. In one embodiment, the invention embraces an isolated, stereochemically pure compound of formula (4), optionally additionally comprising a pharmaceutically acceptable excipient or carrier, and optionally additionally comprising one or more other therapeutic agents. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In one embodiment, the invention embraces an isolated compound of formula (5), optionally additionally comprising a pharmaceutically acceptable excipient or carrier, and optionally additionally comprising one or more other therapeutic agents. In one embodiment, the invention embraces a stereochemically pure compound of formula (5), optionally additionally comprising a pharmaceutically acceptable excipient or carrier, and optionally additionally comprising one or more other therapeutic agents. In one embodiment, the invention embraces an isolated, stereochemically pure compound of formula (5), optionally additionally comprising a pharmaceutically acceptable excipient or carrier, and optionally additionally comprising one or more other therapeutic agents. The foregoing embodiments may optionally also add the proviso that the one or more other therapeutic agents is not another compound of Formula (I) and/or Formula (II).

In one embodiment, the invention embraces an isolated compound of formula (6), optionally additionally comprising a pharmaceutically acceptable excipient or carrier, and optionally additionally comprising one or more other therapeutic agents. In one embodiment, the invention embraces a stereochemically pure compound of formula (6), optionally additionally comprising a pharmaceutically acceptable excipient or carrier, and optionally additionally comprising one or more other therapeutic agents. In one embodiment, the invention embraces an isolated, stereochemically pure compound of formula (6), optionally additionally comprising a pharmaceutically acceptable excipient or carrier, and optionally additionally comprising one or more other therapeutic agents. The foregoing embodiments may optionally also add the proviso that the one or more other therapeutic agents is not another compound of Formula (I) and/or Formula (II).

In one embodiment, the invention embraces an isolated compound of formula (7), optionally additionally comprising a pharmaceutically acceptable excipient or carrier, and optionally additionally comprising one or more other therapeutic agents. In one embodiment, the invention embraces a stereochemically pure compound of formula (7), optionally additionally comprising a pharmaceutically acceptable excipient or carrier, and optionally additionally comprising one or more other therapeutic agents. In one embodiment, the invention embraces an isolated, stereochemically pure compound of formula (7), optionally additionally comprising a pharmaceutically acceptable excipient or carrier, and optionally additionally comprising one or more other therapeutic agents. The foregoing embodiments may optionally also add the proviso that the one or more other therapeutic agents is not another compound of Formula (I) and/or Formula (II).

In one embodiment, the invention embraces an isolated compound of formula (8), optionally additionally comprising a pharmaceutically acceptable excipient or carrier, and optionally additionally comprising one or more other therapeutic agents. In one embodiment, the invention embraces a stereochemically pure compound of formula (8), optionally additionally comprising a pharmaceutically acceptable excipient or carrier, and optionally additionally comprising one or more other therapeutic agents. In one embodiment, the invention embraces an isolated, stereochemically pure compound of formula (8), optionally additionally comprising a pharmaceutically acceptable excipient or carrier, and optionally additionally comprising one or more other therapeutic agents. The foregoing embodiments may optionally also add the proviso that the one or more other therapeutic agents is not another compound of Formula (I) and/or Formula (II).

In another embodiment, the invention comprises a method of treating a muscarinic acetylcholine receptor (mAChR)-mediated disease, comprising administering a therapeutically effective amount of a stereochemically pure compound of Formula (I) or Formula (II) to a subject in need of such treatment. In one embodiment of the method, the compound administered is (1), that is, the compound is (1S,2R)-2-((R)-2'-cyclopentyl-2'-hydroxy 2'-phenylacetoxy)-7,7-dimethyl-7-azoniabicyclo[2.2.1]heptane bromide. In further embodiments of the method, the compound (1) is isolated, and optionally combined with a pharmaceutically acceptable excipient. In further embodiments of the method, the compound (1) is stereochemically pure, and optionally combined with a pharmaceutically acceptable excipient. In further embodiments of the method, the compound (1) is isolated and stereochemically pure. In further embodiments of the method, the compound (1) is isolated and stereochemically pure, and is combined with a pharmaceutically acceptable excipient. In one embodiment of the method, the compound administered is (2), that is, the compound is (1R,2S)-2-((R)-2'-cyclopentyl-2'-hydroxy 2'-phenylacetoxy)-7,7-dimethyl-7-azoniabicyclo[2.2.1]heptane bromide. In further embodiments of the method, the compound (2) is isolated, and optionally combined with a pharmaceutically acceptable excipient. In further embodiments of the method, the compound (2) is stereochemically pure, and optionally combined with a pharmaceutically acceptable excipient. In further embodiments of the method, the compound (2) is isolated and stereochemically pure. In further embodiments of the method, the compound (2) is isolated and stereochemically pure, and is combined with a pharmaceutically acceptable excipient. In one embodiment of the method, the compound administered is (3), that is, the compound is (1R,2R)-2-((R)-2'-cyclopentyl-2'-hydroxy 2'-phenylacetoxy)-7,7-dimethyl-7-azoniabicyclo[2.2.1]heptane bromide. In further embodiments of the method, the compound (3) is isolated, and optionally combined with a pharmaceutically acceptable excipient. In further embodiments of the method, the compound (3) is stereochemically pure, and optionally combined with a pharmaceutically acceptable excipient. In further embodiments of the method, the compound (3) is isolated and stereochemically pure. In further embodiments of the method, the compound (3) is isolated and stereochemically pure, and is combined with a pharmaceutically acceptable excipient. In one embodiment of the method, the compound administered is (4), that is, the compound is (1S,2S)-2-((R)-2'-cyclopentyl-2'-hydroxy 2'-phenylacetoxy)-7,7-dimethyl-7-azoniabicyclo[2.2.1]heptane bromide. In further embodiments of the method, the compound (4) is isolated, and optionally combined with a pharmaceutically acceptable excipient. In further embodiments of the method, the compound (4) is stereochemically pure, and optionally combined with a pharmaceutically acceptable excipient. In further embodiments of the method the compound (4) is isolated and stereochemically pure. In further embodiments of the method, the compound (4) is isolated and stereochemically pure, and is combined with a pharmaceutically acceptable excipient. In one embodiment of the method, the compound administered is (5), that is, the compound is (1R,2S)-2-((S)-2'-cyclopentyl-2'-hydroxy 2'-phenylacetoxy)-7,7-dimethyl-7-azoniabicyclo[2.2.1]heptane bromide. In further embodiments of the method, the compound (5) is isolated, and optionally combined with a pharmaceutically acceptable excipient. In further embodiments of the method, the compound (5) is stereochemically pure, and optionally combined with a pharmaceutically acceptable excipient. In further embodiments of the method, the compound (5) is isolated and stereochemically pure. In further embodiments of the method, the compound (5) is isolated and stereochemically pure, and is combined with a pharmaceutically acceptable excipient. In one embodiment of the method, the compound administered is (6), that is, the compound is (1R,2R)-2-((S)-2'-cyclopentyl-2'-hydroxy 2'-phenylacetoxy)-7,7-dimethyl-7-azoniabicyclo[2.2.1]heptane bromide. In further embodiments of the method, the compound (6) is isolated, and optionally combined with a pharmaceutically acceptable excipient. In further embodiments of the method, the compound (6) is stereochemically pure, and optionally combined with a pharmaceutically acceptable excipient. In further embodiments of the method, the compound (6) is isolated and stereochemically pure. In further embodiments of the method, the compound (6) is isolated and stereochemically pure, and is combined with a pharmaceutically acceptable excipient. In one embodiment of the method, the compound administered is (7), that is, the compound is (1S,2R)-2-((S)-2'-cyclopentyl-2'-hydroxy 2'-phenylacetoxy)-7,7-dimethyl-7-azoniabicyclo[2.2.1]heptane bromide. In further embodiments of the method, the compound (7) is isolated, and optionally combined with a pharmaceutically acceptable excipient. In further embodiments of the method, the compound (7) is stereochemically pure, and optionally combined with a pharmaceutically acceptable excipient. In further embodiments of the method, the compound (7) is isolated and stereochemically pure. In further embodiments of the method, the compound (7) is isolated and stereochemically pure, and is combined with a pharmaceutically acceptable excipient. In one embodiment of the method, the compound administered is (8), that is, the compound is (1S,2S)-2-((S)-2'-cyclopentyl-2'-hydroxy 2'-phenylacetoxy)-7,7-dimethyl-7-azoniabicyclo[2.2.1]heptane bromide. In further embodiments of the method, the compound (8) is isolated, and optionally combined with a pharmaceutically acceptable excipient. In further embodiments of the method, the compound (8) is stereochemically pure, and optionally combined with a pharmaceutically acceptable excipient. In further embodiments of the method, the compound (8) is isolated and stereochemically pure. In further embodiments of the method, the compound (8) is isolated and stereochemically pure, and is combined with a pharmaceutically acceptable excipient. In any of the above embodiments, the composition may optionally additionally comprise one or more other therapeutic agents; such embodiments may optionally also add the proviso that the one or more other therapeutic agents is not another compound of Formula (I) and/or Formula (II).

In another embodiment, the invention comprises a method of suppressing a muscarinic acetylcholine receptor (mAChR)-mediated disease, by administering an amount of one or more compounds of Formula (I) or Formula (II) sufficient to partially or totally suppress the disease to a subject in need of such treatment. In one embodiment of the method, the compound administered is (1), that is, the compound is (1S,2R)-2-((R)-2'-cyclopentyl-2'-hydroxy 2'-phenylacetoxy)-7,7-dimethyl-7-azoniabicyclo[2.2.1]heptane bromide. In further embodiments of the method, the compound (1) is isolated and stereochemically pure. In further embodiments of the method, the compound (1) is isolated and stereochemically pure, and is combined with a pharmaceutically acceptable excipient. In one embodiment of the method, the compound administered is (2), that is, the compound is (1R,2S)-2-((R)-2'-cyclopentyl-2'-hydroxy 2'-phenylacetoxy)-7,7-dimethyl-7-azoniabicyclo[2.2.1]heptane bromide. In further embodiments of the method, the compound (2) is isolated and stereochemically pure. In further embodiments of the method, the compound (2) is isolated and stereochemically pure, and is combined with a pharmaceutically acceptable excipient. In one embodiment of the method, the compound administered is (3), that is, the compound is (1R,2R)-2-((R)-2'-cyclopentyl-2'-hydroxy 2'-phenylacetoxy)-7,7-dimethyl-7-azoniabicyclo[2.2.1]heptane bromide. In further embodiments of the method, the compound (3) is isolated and stereochemically pure. In further embodiments of the method, the compound (3) is isolated and stereochemically pure, and is combined with a pharmaceutically acceptable excipient. In one embodiment of the method, the compound administered is (4), that is, the compound is (1S,2S)-2-((R)-2'-cyclopentyl-2'-hydroxy 2'-phenylacetoxy)-7,7-dimethyl-7-azoniabicyclo[2.2.1]heptane bromide. In further embodiments of the method the compound (4) is isolated and stereochemically pure. In further embodiments of the method, the compound (4) is isolated and stereochemically pure, and is combined with a pharmaceutically acceptable excipient. In one embodiment of the method, the compound administered is (5), that is, the compound is (1R,2S)-2-((S)-2'-cyclopentyl-2'-hydroxy 2'-phenylacetoxy)-7,7-dimethyl-7-azoniabicyclo[2.2.1]heptane bromide. In further embodiments of the method, the compound (5) is isolated and stereochemically pure. In further embodiments of the method, the compound (5) is isolated and stereochemically pure, and is combined with a pharmaceutically acceptable excipient. In one embodiment of the method, the compound administered is (6), that is, the compound is (1R,2R)-2-((S)-2'-cyclopentyl-2'-hydroxy 2'-phenylacetoxy)-7,7-dimethyl-7-azoniabicyclo[2.2.1]heptane bromide. In further embodiments of the method, the compound (6) is isolated and stereochemically pure. In further embodiments of the method, the compound (6) is isolated and stereochemically pure, and is combined with a pharmaceutically acceptable excipient. In one embodiment of the method, the compound administered is (7), that is, the compound is (1S,2R)-2-((S)-2'-cyclopentyl-2'-hydroxy 2'-phenylacetoxy)-7,7-dimethyl-7-azoniabicyclo[2.2.1]heptane bromide. In further embodiments of the method, the compound (7) is isolated and stereochemically pure. In further embodiments of the method, the compound (7) is isolated and stereochemically pure, and is combined with a pharmaceutically acceptable excipient. In one embodiment of the method, the compound administered is (8), that is, the compound is (1S,2S)-2-((S)-2'-cyclopentyl-2'-hydroxy 2'-phenylacetoxy)-7,7-dimethyl-7-azoniabicyclo[2.2.1]heptane bromide. In further embodiments of the method, the compound (8) is isolated and stereochemically pure. In further embodiments of the method, the compound (8) is isolated and stereochemically pure, and is combined with a pharmaceutically acceptable excipient. In any of the above embodiments, the composition may optionally additionally comprise one or more other therapeutic agents; such embodiments may optionally also add the proviso that the one or more other therapeutic agents is not another compound of Formula (I) and/or Formula (II).

In any of the above methods, the muscarinic acetylcholine receptor (mAChR)-mediated disease can be selected from the group consisting of respiratory tract disorders such as chronic obstructive pulmonary disorder (COPD, also called chronic obstructive lung disease), chronic bronchitis, asthma, chronic respiratory obstruction, pulmonary fibrosis, pulmonary emphysema, rhinorrhea, allergic rhinitis, occupational lung diseases including pneumoconiosis (such as black lung disease, silicosis and asbestosis), acute lung injury (ALI), acute respiratory distress syndrome (ARDS), genitourinary tract disorders, such as urinary urge incontinence, overactive bladder or detrusor hyperactivity and their symptoms; gastroesophageal reflux disease (GERD); gastrointestinal tract disorders, such as irritable bowel syndrome, diverticular disease, achalasia, gastrointestinal hypermotility disorders and diarrhea; and the like.

In another embodiment, the invention embraces a composition consisting essentially of a mixture of (1) and (4) in any proportion, such as a 1:1 proportion. In another embodiment, the invention embraces a composition consisting essentially of a mixture of (2) and (3) in any proportion, such as a 1:1 proportion. In another embodiment, the invention embraces a composition consisting essentially of a mixture of (1) and (2) in any proportion, such as a 1:1 proportion. In another embodiment, the invention embraces a composition consisting essentially of a mixture of (3) and (4) in any proportion, such as a 1:1 proportion. Any of the foregoing compositions can additionally consist essentially of an optional additional therapeutic agent. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In another embodiment, the invention embraces a composition consisting essentially of a mixture of (1) and (3) in any proportion, such as a 1:1 proportion. In another embodiment, the invention embraces a composition consisting essentially of a mixture of (2) and (4) in any proportion, such as a 1:1 proportion. Any of the foregoing compositions can additionally consist essentially of an optional additional therapeutic agent. The foregoing embodiments may optionally also add the proviso that the one or more other therapeutic agents exclude(s) compounds (5), (6), (7), and/or (8) as defined herein, or an alternate salt thereof. The foregoing embodiments may optionally also add the proviso that the one or more other therapeutic agents is not another compound of Formula (I) and/or Formula (II).

In another embodiment, the invention comprises a compound of the formula

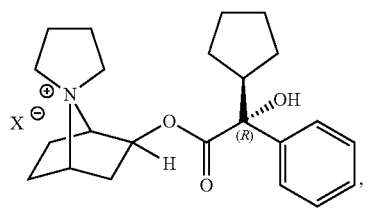

exo-2-((R)-2'-cyclopentyl-2'-hydroxy-2'-phenylacetoxy) spiro[bicyclo-[2.2.1]heptane-7,1'-pyrrolidin]-1'-ium anion, where the anion $X^-$ is a pharmaceutically acceptable anion.

In another embodiment, the invention comprises a compound of the formula

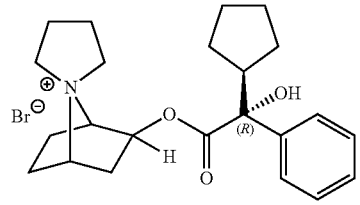

(exo-2-((R)-2'-cyclopentyl-2'-hydroxy-2'-phenylacetoxy) spiro[bicyclo-[2.2.1]heptane-7,1'-pyrrolidin]-1'-ium bromide (9)).

In another embodiment, the invention comprises a composition comprising the compound (9) and a pharmaceutically acceptable excipient or carrier, and optionally additionally comprising one or more other therapeutic agents. In one embodiment, the composition comprising the compound (9) and a pharmaceutically acceptable excipient or carrier also comprises one or more compounds selected from (1), (2), (3), (4), (5), (6), (7), or (8).

The invention also embraces a method of using the compound (9), either alone or in combination with other agents, and optionally comprising a pharmaceutically acceptable excipient or carrier, for treating a variety of indications, including but not limited to diseases mediated by muscarinic acetylcholine receptors. The invention also embraces a method of using the compound (9), either alone or in combination with other agents, and optionally comprising a pharmaceutically acceptable excipient or carrier, for treating respiratory tract disorders such as chronic obstructive pulmonary disorder (COPD, also called chronic obstructive lung disease), chronic bronchitis, asthma, chronic respiratory obstruction, pulmonary fibrosis, pulmonary emphysema, rhinorrhea, allergic rhinitis, occupational lung diseases including pneumoconiosis (such as black lung disease, silicosis and asbestosis), acute lung injury (ALI), and acute respiratory distress syndrome (ARDS). Other, non-respiratory medical conditions that can be treated with muscarinic receptor antagonists include, but are not limited to, genitourinary tract disorders, such as urinary urge incontinence, overactive bladder or detrusor hyperactivity and their symptoms; gastroesophageal reflux disease (GERD); gastrointestinal tract disorders, such as irritable bowel syndrome, diverticular disease, achalasia, gastrointestinal hypermotility disorders and diarrhea; and the like.

Some embodiments described herein are recited as "comprising" or "comprises" various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein.

DETAILED DESCRIPTION OF THE INVENTION

Figure 1:
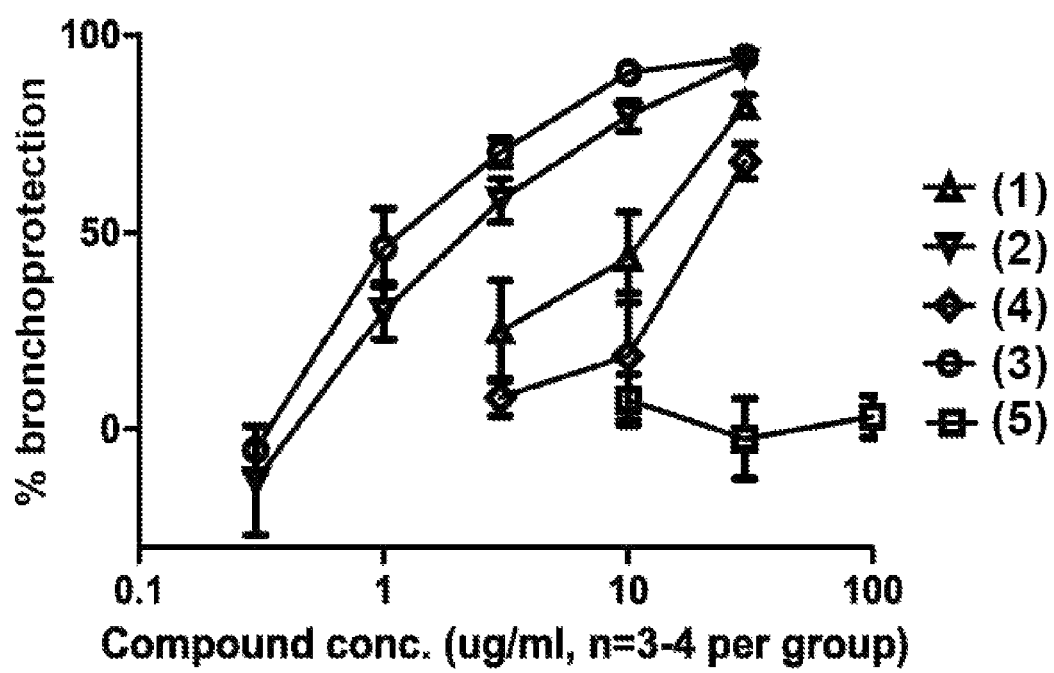
FIG. 1 depicts the percentage of bronchoprotection in rats provided by certain compounds of the invention.

The invention provides compounds and methods for treating a muscarinic acetylcholine receptor-mediated disease, such as chronic obstructive pulmonary disease (COPD).

Definitions

By "subject," "individual," or "patient" is meant an individual organism, preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. The compounds and methods of the invention can be administered to asymptomatic patients at risk of developing the clinical symptoms of the disease, in order to suppress the appearance of any adverse symptoms.

"Therapeutic use" of the compounds discussed herein is defined as using one or more of the compounds discussed herein to treat or suppress a disease, as defined above. A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations.

"Alkyl" is intended to embrace a saturated linear, branched, cyclic, or a combination of linear and/or branched and/or cyclic hydrocarbon chain and/or ring of carbon atoms. In one embodiment, alkyl groups have between 1 and 12 carbon atoms, that is, $C_1$-$C_{12}$ alkyl. In another embodiment, alkyl groups have between 1 and 8 carbon atoms, that is, $C_1$-$C_8$ alkyl. The point of attachment of the alkyl group to the remainder of the molecule can be at any chemically feasible location on the fragment.

"Alkoxy" refers to the group —O-alkyl, for example, —O—$C_1$-$C_{12}$ alkyl or —O—$C_1$-$C_8$ alkyl.

"Lower alkyl" is synonymous with "$C_1$-$C_4$ alkyl," and is intended to embrace methyl (Me), ethyl (Et), propyl (Pr), n-propyl (nPr), isopropyl (iPr), butyl (Bu), n-butyl (nBu), isobutyl (iBu), sec-butyl (sBu), t-butyl (tBu), cyclopropyl (cyclPr), cyclobutyl (cyclBu), cyclopropyl-methyl (cyclPr-Me) and methyl-cyclopropane (Me-cyclPr), where the $C_1$-$C_4$ alkyl groups can be attached via any valence on the $C_1$-$C_4$ alkyl groups to the remainder of the molecule.

"Halo" refers to F, Cl, Br and I.

"Aryl" refers to an aromatic hydrocarbon, such as $C_6$-$C_{10}$ aromatic hydrocarbons including, but not limited to, phenyl and naphthyl.

"Aryloxy" refers to the group —O-aryl.

"Aralkyl" refers to the group -alkyl-aryl.

"Aryloxyalkyl" refers to the group -alkyl-O-aryl.

"Alkoxycarbonylalkyl" refers to the group -alkyl-(C=O)—O-alkyl.

By "isolated" is meant a compound that has been purified in the chemical sense of reducing unwanted components. Isolation can be about 80% pure or at least about 80% pure, about 90% pure or at least about 90% pure, about 95% pure or at least about 95% pure, about 98% pure or at least about 98% pure, about 99% pure or at least about 99% pure, about 99.5% pure or at least about 99.5% pure, or about 99.9% pure or at least about 99.9% pure. Isolation percentages are preferably weight percent, but can also be mole percent. Components that are desired, such as pharmaceutically acceptable excipients, pharmaceutical carriers, or additional therapeutic agents, are not included when calculating the percentage of purity of isolation.

By "stereochemically pure compound" is meant a preparation of a compound which contains primarily one stereoisomer out of two or more possible stereoisomers. A stereochemically pure compound has about 80% or at least about 80% of a single stereoisomer, about 90% or at least about 90% of a single stereoisomer, about 95% or at least about 95% of a single stereoisomer, about 98% or at least about 98% of a single stereoisomer, about 99% or at least about 99% of a single stereoisomer, about 99.5% or at least about 99.5% of a single stereoisomer, or about 99.9% or at least about 99.9% of a single stereoisomer. Stereochemical purity percentages are preferably mole percent, but can also be weight percent. Reference to a particular stereoisomer of a compound as stereochemically pure, or to a composition comprising, consisting essentially of, or consisting of a stereochemically pure compound, means that the preparation of the compound has about 80% or at least about 80% of the referenced stereoisomer, about 90% or at least about 90% of the referenced stereoisomer, about 95% or at least about 95% of the referenced stereoisomer, about 98% or at least about 98% of the referenced stereoisomer, about 99% or at least about 99% of the referenced stereoisomer, about 99.5% or at least about 99.5% of the referenced stereoisomer, or about 99.9% or at least about 99.9% of the referenced stereoisomer.

As an example, the percent isolation of L-alanine, the desired component, in a mixture containing 25 mg of beta-alanine, 25 mg of D-alanine, and 50 mg of L-alanine, where beta-alanine and D-alanine are undesired components, would be 50%. The percent stereochemical purity of L-alanine in that same mixture would be 66.7%, calculated with respect to the total of all stereoisomers of 2-amino propanoic acid (i.e., alanine; beta-alanine is 3-amino propanoic acid and is not a stereoisomer of alanine). (All three molecules have the same molecular weight, and percent by weight and mole percent both yield the same percentages in this example.) Addition of, for example, 1 gram of pharmaceutically acceptable carrier and 50 mg of Vitamin C (where the pharmaceutically acceptable carrier and Vitamin C are desired additional components of the composition) would not affect the percent isolation or percent stereochemical purity calculated for L-alanine.

The terms "active M3 muscarinic acetylcholine receptor antagonist" and "active M3 mAChR antagonist" are synonymous and are used to designate a compound having an $IC_{50}$ of less than 5 nanomolar or less than about 5 nanomolar, preferably less than 3 nanomolar or less than about 3 nanomolar, more preferably less than 1 nanomolar or less than about 1 nanomolar, still more preferably less than 0.5 nanomolar or less than about 0.5 nanomolar, and yet still more preferably less than 0.3 nanomolar or less than about 0.3 nanomolar, as measured by the Muscarinic Receptor Radioligand Binding Assay described below in Example 2.

"An alternate salt thereof," when referring to a compound, indicates that the counterion of the compound may be replaced with another counterion. For example, possible alternate salts of compound (5), (1R,2S)-2-((S)-2'-cyclopentyl-2'-hydroxy 2'-phenylacetoxy)-7,7-dimethyl-7-azoniabicyclo[2.2.1]heptane bromide, include the corresponding chloride: (1R,2S)-2-((S)-2'-cyclopentyl-2'-hydroxy 2'-phenylacetoxy)-7,7-dimethyl-7-azoniabicyclo[2.2.1]heptane chloride; the corresponding tosylate: (1R,2S)-2-((S)-2'-cyclopentyl-2'-hydroxy 2'-phenylacetoxy)-7,7-dimethyl-7-azoniabicyclo[2.2.1]heptane toluenesulfonate; etc.

"Consisting essentially of" as used herein is intended as a limitation to the specified materials or steps recited, and also allows inclusion of any unrecited materials or steps that do not materially affect the basic characteristics of the composition or method. Thus, a composition consisting essentially of compound (1) would exclude any other mAChR antagonist compound, such as compounds (2)-(8), from being present in the mixture, but one or more pharmaceutically acceptable excipients or carriers suitable for the intended route of administration (e.g., a pharmaceutically acceptable excipient or carrier for administration via inhalation, a pharmaceutically acceptable excipient or carrier for administration via injection, or a pharmaceutically acceptable excipient or carrier for administration via oral administration) would not be excluded from a composition consisting essentially of compound (1), even if such a pharmaceutically acceptable excipient or carrier is not explicitly recited.

It should be appreciated that the structures depicted in Formula (I) and Formula (II) represent at least four possible stereoisomers incorporating the four possible isomers of the 7-azabicyclo[2.2.1]heptan-2-ol moieties as illustrated.

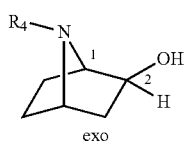
exo (1R,2S)

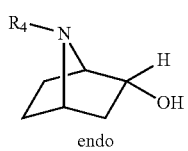
endo (1R,2R)

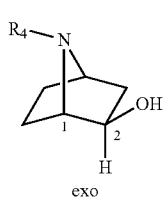
exo (1S,2R)

-continued

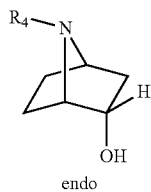
endo (1S,2S)

If additional stereo centers are present, for example, if for the group —C(R$_1$)(R$_2$)(R$_3$), the carbon atom substituted by R$_1$, R$_2$, and R$_3$ is asymmetric, a total of at least eight different diastereomers will result.

If the R$_4$ and R$_5$ groups are different, additional stereoisomers may be generated in the quaternization step.

Included in the scope of this invention are all active isomers, mixtures of active isomers, crystalline forms, amorphous forms, hydrates, or solvates of the subject compounds.

The chemical structures drawn herein and the chemical names listed herein are to be construed as including all isotopologues. Isotopologues are molecular entities that differ only in isotopic composition (number of isotopic substitutions), e.g. CH$_4$, CH$_3$D, CH$_2$D$_2$, etc., where "D" is deuterium, that is, H. Isotopologues can have isotopic replacements at any or at all atoms in a structure, or can have atoms present in natural abundance at any or all locations in a structure.

Various embodiments of the invention described herein are recited as "comprising" or "comprises" various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein.

Methods of Preparation

The compounds of Formula (I) and Formula (II) may be obtained by applying the appropriate synthetic procedures, some of which are illustrated in the scheme below which is for illustrative purposes only.

As outlined in Scheme 1, the desired compounds of Formula (I) and certain compounds of Formula (II) can be prepared by transesterification of ester 1 with the appropriate N-Boc protected amino alcohol 2. Acid treatment of the resulting ester 3 provides the secondary amine 4 which is converted to the tertiary amine 5 by N-alkylation utilizing reductive amination procedures. Finally, quaternization of the tertiary nitrogen of amino ester 5 with an alkyl or aralkyl bromide furnishes the compounds of Formula (I).

Scheme 1

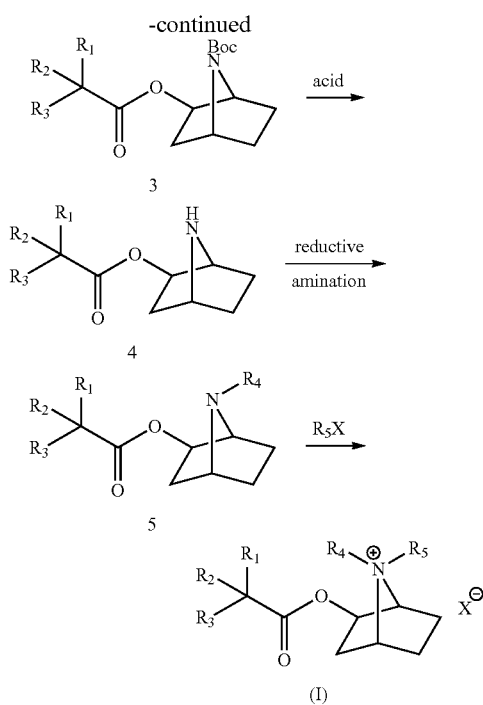

Esters 1 where $R_1$ and $R_2$ are phenyl or 2-thienyl and $R_3$ is OH are commercially available. Esters 1 where $R_1$ is phenyl or thienyl, $R_2$ is cycloalkyl and $R_3$ is OH can be prepared by reaction of an aryl glyoxylate (i.e. PhCOCOOMe) with a cycloalkyl Grignard reagent. Esters where $R_3$ is not OH have also been prepared. The diastereoselective addition of such organometallics to chiral arylglyoxylates leading to optically active products has been described (Tetrahedron Letters 29, 2175 (1988)).

Transesterification of methyl esters 1 with Boc-protected amino alcohols 2 to form the amino esters 3 is carried out using a catalytic amount of a strong base such as sodium hydride, sodium methoxide and the like in a suitable inert solvent such as n-heptane or toluene at temperatures high enough to allow separation of the methanol formed by distillation.

In the case where the group A or $R_1R_2R_3C$ is 10-phenothiazinyl, the desired ester 3 is prepared by reacting 10-chlorocarbonylphenothiazine with amino alcohols 2 in the presence of a base.

Removal of the Boc protection group is achieved by treatment with acid to give the secondary amines 4.

The $R_4$ group, for example methyl, is introduced by reductive amination with formaldehyde and sodium triacetoxyborohydride as described in J. Org. Chem. 61, 3489-3862 (1996) to furnish the tertiary amines 5.

Finally, treatment of the tertiary amines with a compound of formula $R_5X$ in an inert solvent provides the quaternary ammonium compounds of Formula (I).

Spiroazonia compounds where $R_4$ and $R_5$ together form a 5- or 6-membered ring can be prepared from secondary amines 4 by treatment with a dihaloalkane such as 1,4-dichlorobutane or 1,5-dibromopentane in the presence of a base such as triethylamine or potassium carbonate in a suitable solvent.

The methodology described in U.S. Pat. No. 4,353,922 and J. Pharm. Sci. 74, 208-210 (1985) does not provide the compounds of this invention, as these methods provide mixtures of compounds rather than isolated compounds. For example, it was originally thought this methodology produced a mixture of the compounds (3), (4), (6), and (8) described herein. However, more recent research has conclusively demonstrated that the crucial intramolecular epoxide opening step proceeds via an unprecedented cis (not trans) mechanism, leading to the exo amino alcohol intermediates; see J. Org. Chem. 59, 1771-1778 (1994) and Org. Lett. 1, 1439-1441 (1999). Thus, the endo stereochemistry of compound 4 reported in J. Pharm. Sci. 74, 208-210 (1985) (RS-11635, a mixture of four distinct diastereomers rather than a stereochemically pure compound) is incorrect, and compound 4 of J. Pharm. Sci. 74, 208-210 (1985) is in fact a mixture of the compounds (1), (2), (5), and (7) described herein.

The procedures listed in the Examples section demonstrate for the first time how to synthesize all eight possible individual diastereomers of Formula (I) where the carbon atom of the group $R_1R_2R_3C$ is an asymmetric carbon.

Diseases Amenable to Treatment with Compounds of the Invention

The compounds and methods disclosed herein can be used to treat various diseases, particularly diseases mediated by muscarinic acetylcholine receptors. These diseases include, but are not limited to, respiratory tract disorders such as chronic obstructive pulmonary disorder (COPD, also called chronic obstructive lung disease), chronic bronchitis, asthma, chronic respiratory obstruction, pulmonary fibrosis, pulmonary emphysema, rhinorrhea, allergic rhinitis. The diseases also include, but are not limited to, occupational lung diseases including pneumoconiosis (such as black lung disease, silicosis and asbestosis), acute lung injury (ALI), and acute respiratory distress syndrome (ARDS).

Additional, non-respiratory medical conditions that can be treated with muscarinic receptor antagonists include, but are not limited to, genitourinary tract disorders, such as urinary urge incontinence, overactive bladder or detrusor hyperactivity and their symptoms; gastroesophageal reflux disease (GERD); gastrointestinal tract disorders, such as irritable bowel syndrome, diverticular disease, achalasia, gastrointestinal hypermotility disorders and diarrhea; and the like.

Methods of Use

The compounds, pharmaceutical compositions, and methods of the invention can be used in treatment and/or suppression of muscarinic acetylcholine receptor mediated diseases, and in one particular embodiment, in treatment and/or suppression of muscarinic acetylcholine receptor mediated diseases of the respiratory tract. In particular, the compounds, pharmaceutical compositions, and methods of the invention can be used in treating and/or suppressing chronic obstructive pulmonary disorder (COPD), chronic bronchitis, and/or emphysema.

For treatment of respiratory disorders, the compounds and pharmaceutical compositions are preferably administered in a form that can be inhaled, such as in aerosols, mists, sprays, or powders. In one embodiment, the compounds or pharmaceutical compositions are delivered in a form suitable for inhalation. The form suitable for inhalation can be particles, aerosols, powders, or droplets with an average size of about 10 μm diameter or less, preferably in the range between about 0.1 μm to about 5 μm, or in the range between about 1 μm to about 5 μm. See, for example, Hickey, Anthony J., ed., Pharmaceutical Inhalation Aerosol Technology, 2nd Ed., New York: Marcel Dekker, 2004, particularly Part Two on Methods of Generation, Administration, and Characterization of Aerosols. Typically, about two-thirds, preferably 80%, more preferably 90% of the particles, aerosols, powders or droplets will fall within the size range specified. For example, when droplets having a diameter in the range of about 1 μm to about 5 µm are specified, two-thirds, preferably about 80%, more preferably about 90% of the droplets will have a diameter falling in the range of about 1 µm to about 5 µm.

The compounds or pharmaceutical compositions can be delivered in a form suitable for inhalation by using various types of inhalers, such as a nebulizing inhaler, metered-dose inhalers, or a dry powder inhaler (DPI). The compounds or pharmaceutical compositions can be delivered by voluntary inhalation by a subject or patient, or by mechanical ventilation if a subject or patient requires assistance in breathing.

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect. The unit dose may be sufficient as a single dose to have a therapeutic or suppressive effect. Alternatively, the unit dose may be a dose administered periodically in a course of treatment or suppression of a disorder.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), intraocular, subdural, vaginal, rectal, gastrointestinal, and the like, and directly to a specific or affected organ or tissue, such as the lung or bladder. Topical administration may also involve the use of transdermal administration such as transdermal patches or iontophoresis devices. The term parenteral as used herein includes subcutaneous injections, intravenous injection, intramuscular injection, intrasternal injection, or infusion techniques. The compounds are mixed with pharmaceutically acceptable carriers, adjuvants, and vehicles appropriate for the desired route of administration. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

In certain embodiments of the invention, the formulations and preparations of the invention, and the formulations and preparations used in the methods of the invention, are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

The invention also provides articles of manufacture and kits containing materials useful for treating or suppressing muscarinic acetylcholine receptor-mediated diseases. The invention also provides kits comprising any one or more of the compounds of the invention. In some embodiments, the kit of the invention comprises the container described above.

In other aspects, the kits may be used for any of the methods described herein, including, for example, to treat an individual with a muscarinic receptor-mediated disease, or to suppress a muscarinic acetylcholine receptor-mediated disease in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body, or to provide a defined dosage of the drug to a specific site, such as the lungs. The therapeutically effective amount or effective amount for a given situation can be readily determined by routine experimentation and is within the skill and judgment of the ordinary clinician.

Examples of dosages of the compounds described herein which can be used are an effective amount within the dosage range of about 0.1 µg to about 10 mg per kilogram of body weight, about 0.1 µg to about 5 mg per kilogram of body weight, about 0.1 µg to about 1 mg per kilogram of body weight, about 0.1 µg to about 0.5 mg per kilogram of body weight, about 0.1 µg to about 100 µg per kilogram of body weight, about 0.1 µg to about 50 µg per kilogram of body weight, about 0.1 µg to about 10 µg per kilogram of body weight, or about 1 µg to about 10 µg per kilogram of body weight. When administered orally or by inhalation, examples of dosages are an effective amount within the dosage range of about 0.001 mg to about 0.01 mg, or about 0.01 mg to about 0.1 mg, or about 0.1 mg to about 1 mg, or about 1 mg to about 10 mg, or about 10 mg to about 100 mg, or about 100 mg to about 1 g. Preferred fixed doses include about 0.005 mg, about 0.01 mg, about 0.018 mg, about 0.02 mg, about 0.03 mg, about 0.04 mg, about 0.05 mg, about 0.1 mg, about 1 mg, about 2 mg, about 5 mg, about 10 mg, about 20 mg, about 40 mg, about 50 mg, about 80 mg or about 100 mg, independently of body weight. However, it is understand that pediatric patients may require smaller dosages, and depending on the severity of the disease and condition of the patient, dosages may vary. The compound will preferably be administered once daily, but may be administered two, three or four times daily, or every other day, or once or twice per week.

Compounds of the present invention may be administered in a single daily dose, or the total daily dosage may be administered in divided dosage of two, three or four times daily.

When formulated as a liquid, the concentration of the compound described herein will typically be about 0.01 mg/ml to about 0.1 mg/ml or about 0.1 mg/ml to about 1 mg/ml, but can also be about 1 mg/ml to about 10 mg/ml or about 10 mg/ml to about 100 mg/ml. When formulated as a solid, for example as a tablet or as a powder for inhalation, the concentration, expressed as weight compound divided by total weight, will typically be about 0.01% to about 0.1%, about 0.1% to about 1%, about 1% to about 10%, or about 10% to about 100%.

While the compounds of the invention can be administered as the sole active pharmaceutical agent, they can also be used in combination with one or more other agents used in the treatment or suppression of muscarinic acetylcholine receptor-mediated diseases. Examples of additional agents that can be used in combination with the compounds of the current invention include, but are not limited to, other acetylcholine receptor inhibitors, such as ipratropium and tiotropium; or one or more anti-inflammatory, bronchodilator, antihistamine, decongestant or antitussive agents. The additional agents can be administered simultaneously in the same pharmaceutical composition, simultaneously in different pharmaceutical compositions, or at different times. Specific agents include, but are not limited to, corticosteroids such as fluticasone propionate, budesonide, beclomethasone dipropionate, flunisolide, triamcinolone acetonide, ciclesonide, or mometasone furoate; β2-adrenoreceptor agonists such as albuterol, salmeterol, and metaproterenol; antitussive agents (cough suppressants) such as codeine or dextromorphan; and theophylline. Desired combinations can be determined based on additional therapeutic advantages, potential side effects, and other considerations known to the skilled artisan. Some agents can be combined with the compounds of the invention for administration via inhalation, while others can be administered via other routes of administration.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

Compounds of Formula (I) and Formula (II), and compounds (1), (2), (3), (4), (5), (6), (7), or (8), by virtue of the quaternary nitrogen, are positively charged, and thus will have an associated negative counterion. Any pharmaceutically acceptable anion can be used with the compounds of the invention, such as those described in Berge et al., J. Pharm. Sci. 66:1 (1977); Bighley et al., "Salt Forms of Drugs and Absorption," in Swarbrick J, Boylan J C, eds. Encyclopedia of Pharmaceutical Technology 13, New York, N.Y.: Marcel Dekker; 1996:453-499; and Paulekuhn et al., J. Med. Chem. 50:6665 (2007). The anion can be monovalent (i.e., a charge of −1) or polyvalent (e.g., a charge of −2, −3, etc.). Pharmaceutically acceptable anions include, but are not limited to, acetate, besylate (benzenesulfonate), benzoate, besylate, bicarbonate, bitartrate, bromide, calcium edentate, camphorsulfonate (camsylate), carbonate, chloride, chlorotheophyllinate, citrate, edetate, ethanedisulfonate (edisylate), ethanesulfonate (esylate), fumarate, gluceptate (glucoheptonate), gluconate, glucuronate, glutamate, hexylresorcinate, hydroxynaphthoate, hippurate, iodide, isethionate, lactate, lactobionate, lauryl sulfate (estolate), malate, maleate, mandelate, mesylate, methanesulfonate, methylnitrate, methylsulfate, mucate, naphthoate, napsylate, nitrate, octadecanoate, oleate, oxalate, pamoate, pantothenate, phosphate, polygalacturonate, salicylate, stearate, succinate, sulfate, subsalicylate, tannate, tartrate, teoclate, toluenesulfonate (tosylate), and trifluoroacetate. Multiple anions can be used in a single preparation if desired; for example, one micromole of compound (1) can be combined with one-half micromole of chloride ion and one-half micromole of bromide ion.

The compounds of Formula (I) and Formula (II), and compounds (1), (2), (3), (4), (5), (6), (7), or (8), have a single formal positive charge, i.e., they are monovalent cations. The stoichiometry of the anion to the singly-charged (monovalent) cation will depend on the valency of the anion; e.g., when the anion is a monovalent anion, such as Br—, the cation:anion ratio will be 1:1; when the anion is a divalent anion, such as sulfate ($SO_4^{2-}$), the cation:anion ratio will be 2:1, and so forth.

EXAMPLES

Example 1

Synthetic Methods

Example 1.1

(±)-exo-7-[(tert-butoxycarbonyl]-7-azabicyclo[2.2.1]heptan-2-ol and (±)-endo-7-[(tert-butoxycarbonyl]-7-azabicyclo[2.2.1]heptan-2-ol

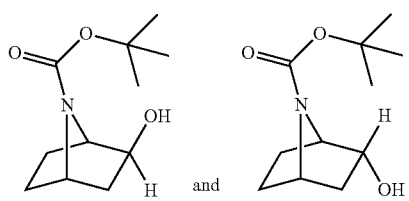

Palladium on carbon (10%, 1.55 g) and ammonium formate (2.48 g, 39.3 mmol) were added to a stirred solution of the combined alcohols (±)-exo-7-(phenylmethyl)-7-azabicyclo[2.2.1]heptan-2-ol and (±)-endo-7-(phenylmethyl)-7-azabicyclo[2.2.1]heptan-2-ol (1.55 g, 7.63 mmol) in dry methanol (51 mL). The resulting suspension was stirred at reflux temperature for 20-30 min. After completion, the catalyst was removed by filtration through a pad of Celite, which was then washed several times with methanol. The filtrate was concentrated in vacuo and to the residue was added anhydrous tetrahydrofuran (17 mL) followed by di-tert-butyl dicarbonate (2.0 g, 9.16 mmol). The reaction mixture was stirred at room temperature for 3 hrs and the solvent was concentrated in vacuo. The residue was taken up with methylene chloride and washed with a solution of ammonium hydroxide. The organic phase was dried ($MgSO_4$) and concentrated. The residue was purified by flash column chromatography to give the alcohols (±)-exo-7-[(tert-butoxycarbonyl]-7-azabicyclo[2.2.1]heptan-2-ol and (±)-endo-7-[(tert-butoxycarbonyl]-7-azabicyclo[2.2.1]heptan-2-ol (1.50 g, 95%).

Example 1.2

(±)-7-[tert-butoxycarbonyl]-7-azabicyclo[2.2.1]heptan-2-one

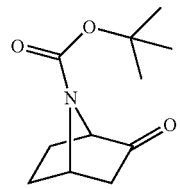

Dess-Martin periodinane (3.83 g, 9.03 mmol) was added in several portions under nitrogen to a stirred solution of the alcohols (±)-exo-7-[(tert-butoxycarbonyl]-7-azabicyclo[2.2.1]heptan-2-ol and (±)-endo-7-[(tert-butoxycarbonyl]-7-azabicyclo[2.2.1]heptan-2-ol (1.50 g, 7.04 mmol) in anhydrous methylene chloride (125 mL). The reaction mixture was stirred overnight at room temperature. After removal of the solvent in vacuo, the solid residue was triturated with diethyl ether and filtrated. The solid was washed several times with diethyl ether and the filtrate was concentrated in vacuo. The residue was purified by flash column chromatography to give the ketone (±)-7-[tert-butoxycarbonyl]-7-azabicyclo[2.2.1]heptan-2-one (1.06 g, 71%).

Example 1.3

(1S,4'R,5'R)-tert-butyl 4',5'-diphenyl-7-azaspiro[bicyclo[2.2.1]heptane-2,2'-imidazolidine]-7-carboxylate and (1R,4'R,5'R)-tert-butyl 4',5'-diphenyl-7-azaspiro[bicyclo[2.2.1]heptane-2,2'-imidazolidine]-7-carboxylate

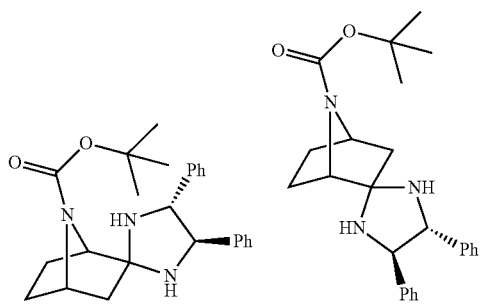 [SMILES: CC(C)(C)OC(=O)N1C2CCC1C1(C2)N[C@H](c2ccccc2)[C@@H](c2ccccc2)N1 ; CC(C)(C)OC(=O)N1C2CCC1C1(C2)N[C@H](c2ccccc2)[C@@H](c2ccccc2)N1]

(R,R)-Diphenylethylenediamine (1.14 g, 5.37 mmol) was added under nitrogen to a solution of ketone (±)-7-[tert-butoxycarbonyl]-7-azabicyclo[2.2.1]heptan-2-one (1.06 g, 5.02 mmol) in dry methylene chloride (17 mL) containing 4 Å molecular sieves. The reaction mixture was stirred at room temperature for 24 h. Triethylamine (2.8 mL) was added and the molecular sieves were then eliminated by filtration. The filtrate was concentrated in vacuo and the resulting residue purified by flash column chromatography (ether/petroleum ether/Et$_3$N, 10:15:1 to 15:10:1) affording first (1S,4'R,5'R)-tert-butyl 4',5'-diphenyl-7-azaspiro[bicyclo[2.2.1]heptane-2,2'-imidazolidine]-7-carboxylate (992 mg, 49%) and then (1R,4'R,5'R)-tert-butyl 4',5'-diphenyl-7-azaspiro-[bicyclo[2.2.1]heptane-2,2'-imidazolidine]-7-carboxylate (0.938 g, 46%).

Example 1.4

(+) (1S)-7-(tert-Butoxycarbonyl)-7-azabicyclo[2.2.1]heptan-2-one

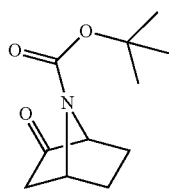

A solution of (1S,4'R,5'R)-tert-butyl 4',5'-diphenyl-7-azaspiro[bicyclo[2.2.1]heptane-2,2'-imidazolidine]-7-carboxylate (992 mg, 2.45 mmol) in 0.1 M H$_3$PO$_4$-THF (2:1, 14.4 mL) was stirred for 30 min at room temperature. The reaction mixture was then diluted with water and extracted with ether. The combined extracts were dried (MgSO$_4$) and the solvent was concentrated in vacuo. The resulting residue was purified by flash column chromatography to give the ketone (+) (1S)-7-(tert-butoxycarbonyl)-7-azabicyclo[2.2.1]heptan-2-one (496 mg, 96%); [α]$^{22}_D$ +74.2° (c 0.43, CHCl$_3$); $^1$H NMR δ (CDCl$_3$, 400 MHz) 4.56 (t, 1H), 4.25 (d, 1H), 2.47 (dd, 1H), 1.99 (m+d, 2+1H), 1.59 (m, 2H), 1.46 (s, 9H).

Example 1.5

(−)-(1R)-7-(tert-Butoxycarbonyl)-7-azabicyclo[2.2.1]heptan-2-one

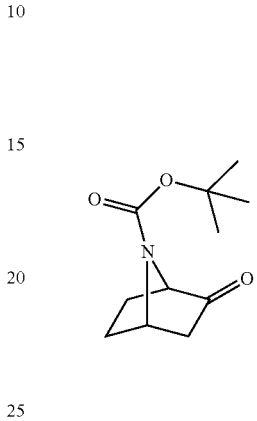

Following the procedure described for the preparation of (+) (1S)-1-(tert-butoxycarbonyl)-7-azabicyclo[2.2.1]heptan-2-one, the diamine (1R,4'R,5'R)-tert-butyl 4',5'-diphenyl-7-azaspiro[bicyclo[2.2.1]heptane-2,2'-imidazolidine]-7-carboxylate (938 mg, 2.31 mmol) was converted to (−) (1R)-7-(tert-Butoxycarbonyl)-7-azabicyclo[2.2.1]heptan-2-one (468 mg, 96%). [α]$^{22}_D$ −58.6° (c 0.11, CHCl$_3$); $^1$H NMR δ (CDCl$_3$, 400 MHz) 4.56 (t, 1H), 4.25 (d, 1H), 2.47 (dd, 1H), 1.99 (m+d, 2+1H), 1.59 (m, 2H), 1.46 (s, 9H).

Example 1.6

(1S,2S)-7-(tert-Butoxycarbonyl)-7-azabicyclo[2.2.1]heptane-2-ol and (1S,2R)-7-(tert-butoxycarbonyl)-7-azabicyclo[2.2.1]heptan-2-ol

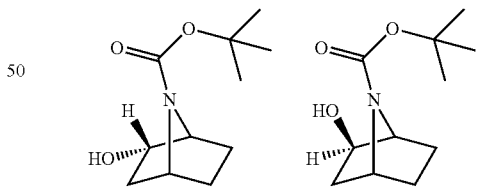

Platinum oxide (27 mg) followed by triethylamine (0.98 mL, 7.05 mmol) were added to a stirred solution of ketone (+) (1S)-7-(tert-Butoxycarbonyl)-7-azabicyclo[2.2.1]heptan-2-one (496 mg, 2.35 mmol) in ethanol (1.2 mL). The flask was purged under vacuum and was then filled with hydrogen using a balloon. The reaction mixture was stirred at room temperature for 48 hours. The catalyst was then removed by filtration through a pad of Celite, which was washed several times with methanol. The filtrate was concentrated in vacuo and the resulting residue was purified by flash column chromatography affording first (1S,2S)-1-(tert-butoxycarbonyl)-

7-azabicyclo[2.2.1]heptan-2-ol (140 mg, 28%) and then (1S,2R)-1-(tert-butoxycarbonyl)-7-azabicyclo[2.2.1]heptan-2-ol (160 mg, 32%).

Example 1.7

(1R,2R)-7-(tert-butoxycarbonyl)-7-azabicyclo[2.2.1]heptan-2-ol and (1R,2S)-1-(tert-butoxycarbonyl)-7-azabicyclo[2.2.1]heptan-2-ol

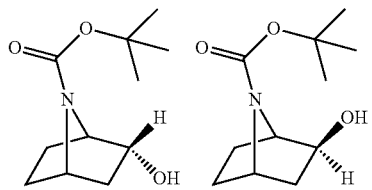

Following the procedure described for the preparation of (1S,2S)-1-(tert-butoxycarbonyl)-7-azabicyclo[2.2.1]heptan-2-ol and (1S,2R)-1-(tert-butoxycarbonyl)-7-azabicyclo[2.2.1]heptan-2-ol, the ketone (–) (1R)-1-(tert-Butoxycarbonyl)-7-azabicyclo[2.2.1]heptan-2-one (468 mg, 2.22 mmol) was converted to (1R,2R)-7-(tert-butoxycarbonyl)-7-azabicyclo[2.2.1]heptan-2-ol (150 mg, 32%) and (1R,2S)-7-(tert-butoxycarbonyl)-7-azabicyclo[2.2.1]heptan-2-ol (140 mg, 30%).

Example 1.8

(1R,2S)-2-((R)-2'-cyclopentyl-2'-hydroxy 2'-phenylacetoxy)-7-(tert-butoxycarbonyl)-7-azabicyclo[2.2.1]heptane

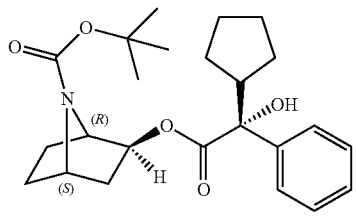

To (1R,2S)-2-hydroxy-7-(tert-butoxycarbonyl)-7-azabicyclo[2.2.1]heptane (68 mg, 0.32 mmol) in 5 mL of heptane was added (R)-methyl-2-cyclopentyl-2-hydroxy 2-phenylacetate (149 mg, 0.64 mmol) followed by cat. NaH (8 mg as a 60% dispersion in oil) and the mixture was stirred at 100° C. for 20 hrs. Water was added and the mixture was extracted with ethyl acetate, dried over sodium sulfate and concentrated. The residue was purified by column chromatography on silica gel using hexane/ethyl acetate as eluent to yield 76 mg of the desired product, (1R,2S)-2-((R)-2'-cyclopentyl-2'-hydroxy 2'-phenylacetoxy)-7-(tert-butoxycarbonyl)-7-azabicyclo[2.2.1]heptane as an oil.

Similarly prepared were:
(1S,2R)-2-((R)-2'-cyclopentyl-2'-hydroxy 2'-phenylacetoxy)-7-(tert-butoxycarbonyl)-7-azabicyclo[2.2.1]heptane,
(1S,2S)-2-((R)-2'-cyclopentyl-2'-hydroxy 2'-phenylacetoxy)-7-(tert-butoxycarbonyl)-7-azabicyclo[2.2.1]heptane,
(1R,2R)-2-((R)-2'-cyclopentyl-2'-hydroxy 2'-phenylacetoxy)-7-(tert-butoxycarbonyl)-7-azabicyclo[2.2.1]heptane,
(1R,2S)-2-((S)-2'-cyclopentyl-2'-hydroxy 2'-phenylacetoxy)-7-(tert-butoxycarbonyl)-7-azabicyclo[2.2.1]heptane,
(1S,2R)-2-((S)-2'-cyclopentyl-2'-hydroxy 2'-phenylacetoxy)-7-(tert-butoxycarbonyl)-7-azabicyclo[2.2.1]heptane,
(1S,2S)-2-((S)-2'-cyclopentyl-2'-hydroxy 2'-phenylacetoxy)-7-(tert-butoxycarbonyl)-7-azabicyclo[2.2.1]heptane, and
(1R,2R)-2-((S)-2'-cyclopentyl-2'-hydroxy 2'-phenylacetoxy)-7-(tert-butoxycarbonyl)-7-azabicyclo[2.2.1]heptane.

Example 1.9

(1R,2S)-2-((R)-2'-cyclopentyl-2'-hydroxy 2'-phenylacetoxy)-7-methyl-7-azabicyclo[2.2.1]heptane

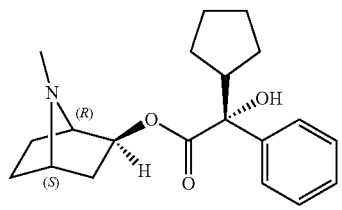

To (1R,2S)-2-((R)-2'-cyclopentyl-2'-hydroxy 2'-phenylacetoxy)-7-(tert-butoxycarbonyl)-7-azabicyclo[2.2.1]heptane (76 mg, 0.182 mmol) was added 1 mL of 4N hydrochloric acid in dioxane and the mixture was stirred at room temperature for 0.5 hr. The dioxane was removed under vacuum and the residue was basified with ammonium hydroxide to pH 10 and extracted with 3×30 mL of methylene chloride. The combined organic layers were dried over sodium sulfate and concentrated to yield the crude amine. To this amine, dissolved in 5 mL of dichloroethane, was added 0.1 mL of formaldehyde solution (37% w/v in water) followed by sodium triacetoxyborohydride (76 mg, 0.364 mmol) and the mixture stirred at room temperature overnight. Water was added and the mixture was extracted with 3×50 mL of methylene chloride. The combined organic layers were dried over sodium sulfate and concentrated to yield the crude tertiary amine which was further purified on silica gel using methylene chloride/methanol/ammonia (90:9:1) as the eluent to yield 46 mg of (1R,2S)-2-((R)-2'-cyclopentyl-2'-hydroxy 2'-phenylacetoxy)-7-methyl-7-azabicyclo[2,2,1]heptane as an oil.

Similarly prepared were:
(1S,2R)-2-((R)-2'-cyclopentyl-2'-hydroxy 2'-phenylacetoxy)-7-methyl-7-azabicyclo[2.2.1]heptane,
(1S,2S)-2-((R)-2'-cyclopentyl-2'-hydroxy 2'-phenylacetoxy)-7-methyl-7-azabicyclo[2.2.1]heptane,
(1R,2R)-2-((R)-2'-cyclopentyl-2'-hydroxy 2'-phenylacetoxy)-7-methyl-7-azabicyclo[2.2.1]heptane,
(1R,2S)-2-((S)-2'-cyclopentyl-2'-hydroxy 2'-phenylacetoxy)-7-methyl-7-azabicyclo[2.2.1]heptane,
(1S,2R)-2-((S)-2'-cyclopentyl-2'-hydroxy 2'-phenylacetoxy)-7-methyl-7-azabicyclo[2.2.1]heptane
(1S,2S)-2-((S)-2'-cyclopentyl-2'-hydroxy 2'-phenylacetoxy)-7-methyl-7-azabicyclo[2.2.1]heptane, and (1R,2R)-2-((S)-2'-cyclopentyl-2'-hydroxy 2'-phenylacetoxy)-7-methyl-7-azabicyclo[2.2.1]heptane.

Example 1.10

(1R,2S)-2-((R)-2'-cyclopentyl-2'-hydroxy 2'-phenylacetoxy)-7,7-dimethyl-7-azoniabicyclo[2.2.1]heptane bromide (2)

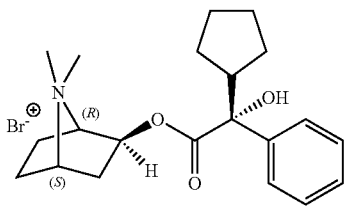

To (1R,2S)-2-((R)-2'-cyclopentyl-2'-hydroxy 2'-phenylacetoxy)-7-methyl-7-azabicyclo[2.2.1]heptane (46 mg, 0.139 mmol) in acetone (2 mL) was added 1 mL of methyl bromide solution (2M in ether). The resulting mixture was left at room temperature for 48 hrs. The crystallized product was filtered off and dried to yield 36 mg of (1R,2S)-2-((R)-2'-cyclopentyl-2'-hydroxy 2'-phenylacetoxy)-7,7-dimethyl-7-azoniabicyclo[2.2.1]heptane bromide (2) as a white crystalline solid, M.P. 233-234° C., $^1$HNMR: 7.6 (dd, 2H); 7.4 (m, 2H); 7.28 (m, 1H); 5.0 (m, 1H); 4.9 (m, 1H); 4.45 (m, 1H); 3.8 (s, 1H); 3.49 (s, 3H); 3.28 (s, 3H); 3.0 (m, 1H); 2.5-2.2 (m, 4H); 1.9-1.3 (m, 10H).

Similarly prepared were:

(1), (1S,2R)-2-((R)-2'-cyclopentyl-2'-hydroxy 2'-phenylacetoxy)-7,7-dimethyl-7-azoniabicyclo[2.2.1]heptane bromide, M.P. 198-200° C., $^1$HNMR: 7.45 (dd, 2H); 7.25 (m, 2H); 7.1 (m, 1H); 5.1 (m, 1H); 4.9 (m, 1H); 4.1 (m, 1H); 3.8 (s, 1H); 3.23 (s, 3H); 3.0 (s, 3H); 2.8 (m, 1H); 2.3 (m, 4H); 2.8-1.2 (m, 10H);

(4), (1S,2S)-2-((R)-2'-cyclopentyl-2'-hydroxy 2'-phenylacetoxy)-7,7-dimethyl-7-azoniabicyclo[2.2.1]heptane bromide, M.P. 210-212° C., $^1$HNMR: 7.59 (d, 2H); 7.36 (t, 2H); 7.3 (m, 1H); 5.4 (m, 1H); 4.8 (m, 1H); 5.6 (m, 1H); 3.6 (s, 1H); 3.5 (s, 6H); 2.85 (m, 2H); 2.2 (m, 2H); 1.8-1.2 (m, 9H);

(3), (1R,2R)-2-((R)-2'-cyclopentyl-2'-hydroxy 2'-phenylacetoxy)-7,7-dimethyl-7-azoniabicyclo[2.2.1]heptane bromide, M.P. 232-233° C., $^1$HNMR: 7.59 (d, 2H); 7.37 (t, 2H); 7.32 (m, 1H); 5.4 (m, 1H); 4.9 (t, 1H); 4.4 (t, 1H); 3.6 (s, 1H); 3.56 (s, 3H); 3.46 (s, 3H); 3.0 (m, 2H); 2.3 (m, 1H); 1.9 (m, 1H); 1.8-1.2 (m, 10H);

(5), (1R,2S)-2-((S)-2'-cyclopentyl-2'-hydroxy 2'-phenylacetoxy)-7,7-dimethyl-7-azoniabicyclo[2.2.1]heptane bromide, M.P. 222-224° C., $^1$HNMR: 7.6 (dd, 2H); 7.4 (m, 2H); 7.28 (m, 1H); 5.0 (m, 1H); 4.9 (m, 1H); 4.45 (m, 1H); 3.8 (s, 1H); 3.49 (s, 3H); 3.28 (s, 3H); 3.0 (m, 1H); 2.5-2.2 (m, 4H); 1.9-1.3 (m, 10H);

(7), (1S,2R)-2-((S)-2'-cyclopentyl-2'-hydroxy 2'-phenylacetoxy)-7,7-dimethyl-7-azoniabicyclo[2.2.1]heptane bromide, M.P. 231-233° C., $^1$HNMR: 7.45 (dd, 2H); 7.25 (m, 2H); 7.1 (m, 1H); 5.1 (m, 1H); 4.9 (m, 1H); 4.1 (m, 1H); 3.8 (s, 1H); 3.23 (s, 3H); 3.0 (s, 3H); 2.8 (m, 1H); 2.3 (m, 4H); 2.8-1.2 (m, 10H);

(8), (1S,2S)-2-((S)-2'-cyclopentyl-2'-hydroxy 2'-phenylacetoxy)-7,7-dimethyl-7-azoniabicyclo[2.2.1]heptane bromide, M.P. 223-225° C., $^1$HNMR: 7.59 (d, 2H); 7.36 (t, 2H); 7.3 (m, 1H); 5.4 (m, 1H); 4.8 (m, 1H); 5.6 (m, 1H); 3.6 (s, 1H); 3.5 (s, 6H); 2.85 (m, 2H); 2.2 (m, 2H); 1.8-1.2 (m, 9H); and (6), (1R,2R)-2-((S)-2'-cyclopentyl-2'-hydroxy 2'-phenylacetoxy)-7,7-dimethyl-7-azoniabicyclo[2.2.1]heptane bromide, M.P. 212-214° C., $^1$HNMR: 7.59 (d, 2H); 7.37 (t, 2H); 7.32 (m, 1H); 5.4 (m, 1H); 4.9 (t, 1H); 4.4 (t, 1H); 3.6 (s, 1H); 3.56 (s, 3H); 3.46 (s, 3H); 3.0 (m, 2H); 2.3 (m, 1H); 1.9 (m, 1H); 1.8-1.2 (m, 10H).

Example 1.11

Exo-2-((R)-2'-cyclopentyl-2'-hydroxy-2'-phenylacetoxy)spiro[bicyclo-[2.2.1]heptane-7,1'-pyrrolidin]-1'-ium bromide (9)

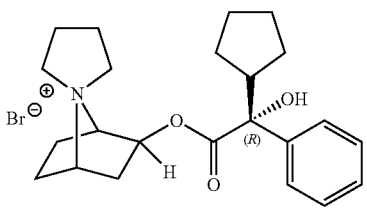

To a solution of Exo-2-((R)-2'-cyclopentyl-2'-hydroxy 2'-phenylacetoxy)-7-azabicyclo[2.2.1]heptane (151 mg, 0.479 mmol) in acetonitrile (3 mL) were added 1,4-dibromobutane (206 mg, 0.958 mmol) and 1,8-diazabicyclo[5.4.0]undec-7-ene (109 mg, 0.717 mmol). The resulting solution was stirred at 60° C. for 20 hrs. The cooled solution was evaporated to dryness and the residual oil was triturated with acetone/ethyl acetate. The resulting solid was recrystallized from acetone/ethyl acetate, filtered off and dried to give 44 mg of the desired product, M.P. 214-217° C., MS 370 (M$^+$).

Example 2

Biological Methods

The antagonist effects of compounds at the M$_3$ mAChR of the present invention are determined by the following in vitro and in vivo assays.

Muscarinic Receptor Radioligand Binding Assay:

Radioligand binding studies were carried out with M$_3$ receptor cell homogenates as described (Peralta et al., The EMBO Journal 6, 3923-3929, (1987)). Incubations of test ligands (or standard) with 0.2 nM [$^3$H]-4-DAMP were incubated for 120 minutes at 22° C. using human M$_3$ receptor-expressing cell homogenates. Specific ligand binding to the receptors was defined as the difference between the total radioligand binding and the nonspecific binding determined in the presence of an excess of unlabelled ligand (10 μM atropine). The results were expressed as a percent of control specific binding ((measured specific binding/control specific binding)×100) obtained in the presence of various concentrations of the test compounds.

The IC$_{50}$ values (concentration causing a half-maximal inhibition of control specific binding) and Hill coefficients (nH) were determined by non-linear regression analysis of the competition curves generated with mean replicate values using Hill equation curve fitting (Y=D+[(A−D)/(1+(C/C$_{50}$)$^{nH}$)], where Y=specific binding, D=minimum specific binding, A=maximum specific binding, C=compound concentration, C$_{50}$=IC$_{50}$, and nH=slope factor).

The inhibition constants (K$_i$) were calculated using the Cheng-Prusoff equation (K$_i$=IC$_{50}$/(1+(L/K$_D$)), where L=concentration of radioligand in the assay, and K$_D$=affinity of the radioligand for the receptor). A Scatchard plot was used to determine the radioligand K$_d$.

When tested by the above method, the compounds of the invention had K$_i$ values in the range of 0.1 to 100 nM, as shown in Table 1.

TABLE 1

| Compound ID | Structure | Test conc. (nM) | M3 (antagonist) % Inhibition of Control Specific Binding | IC$_{50}$ (nM) | K$_i$ (nM) |
|---|---|---|---|---|---|
| (1) | 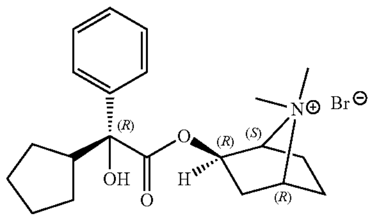 | 10 | 100 | 0.23 | 0.16 |
| (2) | 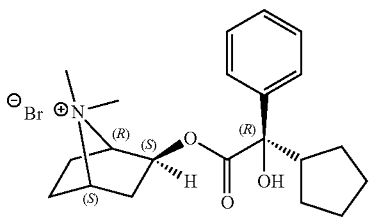 | 10 | 98 | 0.25 | 0.18 |
| (3) | 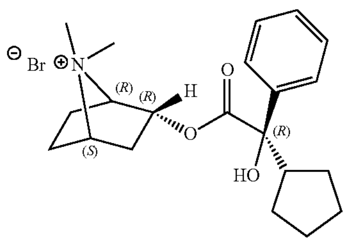 | 10 | 99 | 0.25 | 0.18 |
| (4) | 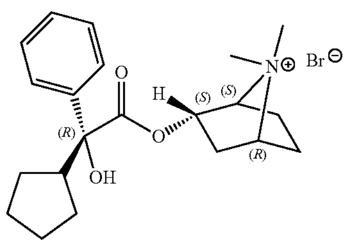 | 10 | 100 | 0.3 | 0.22 |
| (5) | 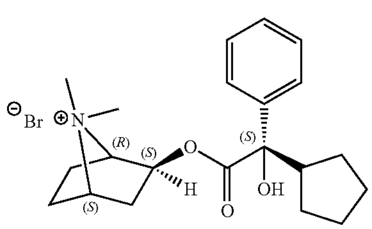 | 10 | 80 | 2.1 | 1.5 |
| (6) | 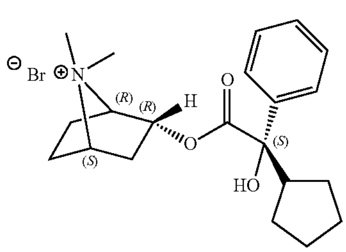 | 10 | 75 | 2.9 | 2.1 |

TABLE 1-continued

| Compound ID | Structure | Test conc. (nM) | M3 (antagonist) % Inhibition of Control Specific Binding | IC$_{50}$ (nM) | K$_i$ (nM) |
|---|---|---|---|---|---|
| (7) | 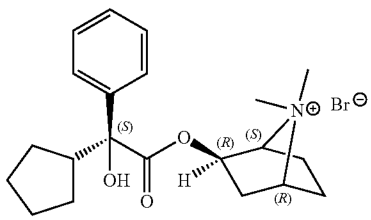 | 10 | 30 | 19 | 14 |
| (8) | 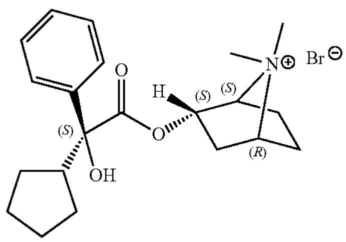 | 10 | 9 | 36 | 26 |

Bronchodilator Potency and Duration of Action Studies; Rat Einthoven Model:

The bronchodilator potency and duration of action studies utilize male Sprague-Dawley rats (200-350 g). Animals are placed in a dosing chamber and exposed to the aerosol generated from an LC Star Nebulizer Set and driven by a mixture of gases (5% $CO_2$, 20% oxygen and 75% nitrogen) by being placed for no more than 30 min in a dosing chamber. Within the dosing chamber the animals are not restrained but are confined to a space that has an approximate floor area of 18 square inches. The animals are acclimated to the chamber for 10 min, then treated with test compounds which are delivered via inhalation. Each test compound solution is nebulized over 5 to 25 minutes. After a predetermined period, based on the time point studied, the animals are evaluated for the pharmacodynamic effects of the test compounds. Thirty minutes prior to the start of pulmonary evaluation, the animals are anesthetized with pentobarbital sodium (Nembutal, 25 mg/kg). The jugular vein is catheterized with saline+10 U/ml heparin-filled polyethylene catheters (PE-20) used to infuse the bronchoconstrictor methacholine (MCh). The carotid artery is cannulated with 10 U/ml heparin/saline-filled PE-50 catheters and connected to a pressure transducer for the measurement of blood pressure and heart rate (CV effects). The trachea is then dissected free and cannulated with a 14G steel tube connected to a pressure transducer for the measurement of pulmonary resistance and to a constant volume rodent respirator set to deliver an appropriate tidal volume and at a rate determined by the animal's weight. This is used for rat ventilation during the evaluation of the pulmonary and CV effects of the test articles. Intravenous MCh is administered at a dose sufficient to cause 80% of the maximal pulmonary constriction in an untreated animal (determined by experimentation in a pilot study using 4 rats). The pulmonary and CV responses to the MCh determine the potency, safety and pharmacodynamic effects of test articles.

Rat Bronchoprotection Protocol-MCh Dose Response:

Test compounds and control (water) were administered to male Sprague Dawley rats (200-350 g) via inhalation. Inhalation dosing was done by placing the rats in a dosing chamber and exposing them for 25 min to nebulized drug solutions using a Pari nebulizer. The animals were then returned to their cages. The chamber was decontaminated between uses by washing with water.

Twenty-four hours after dosing and thirty minutes prior to the start of pulmonary evaluation, the animals were anesthetized with pentobarbital sodium (Nembutal, 50 mg/mL, 1 mL/kg, IP). The trachea was then dissected free and cannulated with a 14G steel tube connected to a pressure transducer (for the measurement of pulmonary inflation pressure) and to a constant volume rodent respirator set to deliver an appropriate tidal volume (2.5 ml) and at a rate determined by the animal's weight (60 breath/min). The carotid artery was cannulated with a 5 U/ml heparin/saline-filled PE-50 cannula and connected to a pressure transducer for the measurement of blood pressure and heart rate. The jugular vein was catheterized with a saline filled polyethylene catheter (PE-10) and used to deliver bolus challenges of the bronchoconstrictor methacholine (MCh). Intravenous ascending doses of MCh (1 to 300 μg/kg) were administered, after the response to the previous dose returned to baseline. The pulmonary inflation pressure and blood pressure were recorded using a Biopac system with the AcqKnowledge software. The animals were euthanized upon completion of the study by cervical dislocation followed by a thoracotomy.

The results of the bronchoprotection studies are shown in FIG. 1. Table 2 shows the in vivo potency (24 h post inhalation) and duration of bronchoprotective effects against methacholine-induced bronchoconstriction in rat.

TABLE 2

| Compound ID | Potency (ID$_{50}$) | Duration |
|---|---|---|
| (1) | ≥10 μg/mL | ++ |
| (2) | ≤3 μg/mL | +++ |
| (3) | ≤3 μg/mL | +++ |
| (4) | >10 μg/mL | + |
| (5), (6), (7) & (8) | >100 μg/mL | − |

− inactive 24 h post inhalation
+ <24 h duration
++ ≥24 h duration
+++ ≥48 h duration Bronchodilator Potency and Duration of Action Studies; Guinea Pig Einthoven Model:

The bronchodilator potency and duration of action studies utilize male Dunkin Hartley guinea pigs (250-350 g). Animals are placed in a dosing chamber and exposed to the aerosol generated from an LC Star Nebulizer Set and driven by a mixture of gases (5% $CO_2$, 20% oxygen and 75% nitrogen) by being placed for no more than 30 min in a dosing chamber. Within the dosing chamber the animals are not restrained but are confined to a space that has an approximate floor area of 18 square inches. The animals are acclimated to the chamber for 10 min, then treated with test compounds which are delivered via inhalation. Each test compound solution is nebulized over 5 to 25 minutes. After a predetermined period, based on the time point studied, the animals are evaluated for the pharmacodynamic effects of the test compounds. Thirty minutes prior to the start of pulmonary evaluation, the animals are anesthetized with intramuscular ketamine (55.8 mg/kg), xylazine (3.9 mg/kg) and acepromazine (1 mg/kg). The jugular vein is catheterized with saline+10 U/ml heparin-filled polyethylene catheters (PE-20) used to infuse the bronchoconstrictor methacholine (MCh). The carotid artery is cannulated with 10 U/ml heparin/saline-filled PE-50 catheters and connected to a pressure transducer for the measurement of blood pressure and heart rate (CV effects). The trachea is then dissected free and cannulated with a 14G steel tube connected to a pressure transducer for the measurement of pulmonary resistance and to a constant volume rodent respirator set to deliver an appropriate tidal volume and at a rate determined by the animal's weight. This is used for guinea pig ventilation during the evaluation of the pulmonary and CV effects of the test articles. Intravenous MCh is administered at a dose sufficient to cause 80% of the maximal pulmonary constriction in an untreated animal (determined by experimentation in a pilot study using 4 guinea pigs). The pulmonary and CV responses to the MCh determine the potency, safety and pharmacodynamic effects of test articles.

Guinea Pig Bronchoprotection Protocol-MCh Dose Response:

Test compounds and control (water) were administered to male Dunkin Hartley guinea pigs (250-350 g) via inhalation. Inhalation dosing was done by placing the guinea pigs in a dosing chamber and exposing them for 25 min to nebulized drug solutions using a Pari nebulizer. The animals were then returned to their cages. The chamber was decontaminated between uses by washing with water.

Twenty-four hours after dosing and thirty minutes prior to the start of pulmonary evaluation, the animals were anesthetized with intramuscular ketamine (55.8 mg/kg), xylazine (3.9 mg/kg) and acepromazine (1 mg/kg). The trachea was then dissected free and cannulated with a 14G steel tube connected to a pressure transducer (for the measurement of pulmonary inflation pressure) and to a constant volume rodent respirator set to deliver an appropriate tidal volume (2.5 ml) and at a rate determined by the animal's weight (100 breath/min). The carotid artery was cannulated with a 5 U/ml heparin/saline-filled PE-50 cannula and connected to a pressure transducer for the measurement of blood pressure and heart rate. The jugular vein was catheterized with a saline filled polyethylene catheter (PE-10) and used to deliver bolus challenges of the bronchoconstrictor methacholine (MCh). Intravenous ascending doses of MCh (1 to 300 μg/kg) were administered, after the response to the previous dose returned to baseline. The pulmonary inflation pressure and blood pressure were recorded using a Biopac system with the Acq-Knowledge software. The animals were euthanized upon completion of the study by cervical dislocation followed by a thoracotomy.

Figure 2:
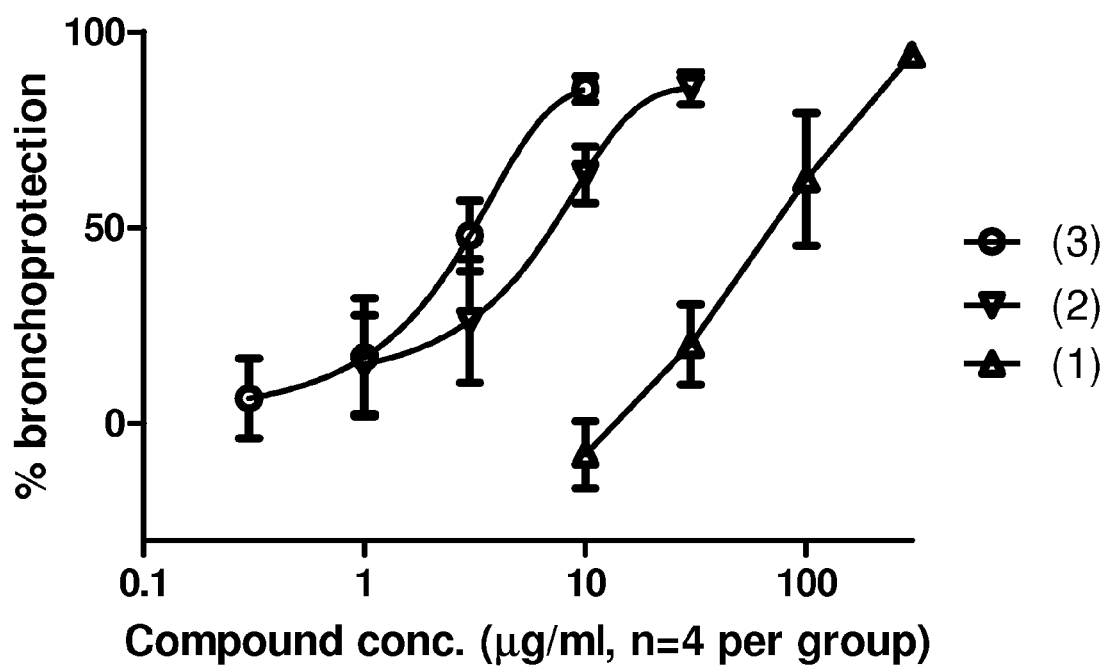
FIG. 2 depicts the percentage of bronchoprotection in guinea pigs provided by certain compounds of the invention.

The results of the bronchoprotection studies are shown in FIG. 2. Table 3 shows in vivo potency (24 h post inhalation) and duration of bronchoprotective effects against methacholine-induced bronchoconstriction in guinea pig.

TABLE 3

| Compound ID | Potency ($ID_{50}$) | Duration |
| --- | --- | --- |
| (1) | 50 μg/mL | +++ |
| (2) | 5 μg/mL | +++ |
| (3) | 3 μg/mL | +++ |

+++ ≥48 h duration

The disclosures of all publications, patents, patent applications and published patent applications referred to herein by an identifying citation are hereby incorporated herein by reference in their entireties for all purposes, to the same extent as if each individual publication, patent, patent application and published patent application was specifically and individually indicated to be incorporated by reference in its entirety, for all purposes.

Although the foregoing invention has been described in some detail by way of illustration and example for purposes of clarity of understanding, it is apparent to those skilled in the art that certain changes and modifications will be practiced. Unless otherwise apparent from the context, any step, element, embodiment, feature or aspect of the invention can be used with any other. Therefore, the description and examples should not be construed as limiting the scope of the invention.

What is claimed is:

1. A stereochemically pure compound with a stereochemical purity of at least 80% according to Formula (II):

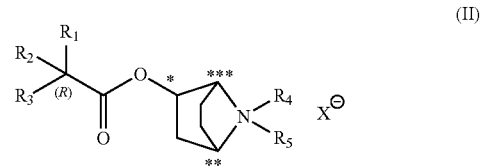

where $R_1$ is independently selected from phenyl or thienyl, both optionally substituted with an alkyl, alkoxy, halo, or COOR group;

where $R_2$ is independently selected from phenyl, thienyl, cyclopentyl, cyclohexyl, 1-alkylcyclopentyl, 1-alkylcyclohexyl, 1-hydroxycyclopentyl or 1-hydroxycyclohexyl, where phenyl, thienyl, cyclopentyl, cyclohexyl, 1-alkylcyclopentyl, 1-alkylcyclohexyl,1-hydroxycyclopentyl or 1-hydroxycyclohexyl are optionally substituted with an alkyl, alkoxy, halo, or COOR group;

or where $R_1$ and $R_2$ together are 9-xanthenyl, where 9-xanthenyl is substituted on either or both benzene rings with an alkyl, alkoxy, halo, or COOR group;

where $R_3$ is OH;

$R_4$ and $R_5$ are independently selected from lower alkyl, alkoxycarbonylalkyl, aralkyl, or aryloxyalkyl, where alkoxycarbonylalkyl and/or aralkyl are optionally substituted with an alkyl, alkoxy, halo, or COOR group;

or $R_4$ and $R_5$ together with the ring to which they are attached form a five- or six-membered ring optionally substituted with aryl or aryloxy;

where R is a lower alkyl;

where *, , and * are each independently a stereocenter, and wherein the stereocenters *, **, and

*** are present in one of the following combinations:
  (i) * is (R),  is (R), and * is (S), or
  (ii) * is (S),  is (S), and * is (R), or
  (iii) * is (R),  is (S), and * is (R)
  (iv) * is (S),  is (R), and * is (S); and $X^\ominus$ represents a pharmaceutically acceptable anion.

2. A compound according to claim 1, wherein $R_1$ is phenyl, optionally substituted with an alkyl, alkoxy, halo, or COOR group.

3. A compound according to claim 2, wherein $R_1$ is unsubstituted phenyl.

4. A compound according to claim 1, wherein $R_2$ is cyclopentyl.

5. A compound according to claim 1, where $R_4$ and $R_5$ are independently selected from $C_1$-$C_4$ alkyl.

6. A compound according to claim 5, wherein both $R_4$ and $R_5$ are methyl.

7. The compound of claim 1, where $X^-$ is selected from the group consisting of acetate, besylate (benzenesulfonate), benzoate, bicarbonate, bitartrate, bromide, calcium edetate, camphorsulfonate (camsylate), carbonate, chloride, chlorotheophyllinate, citrate, edetate, ethanedisulfonate (edisylate), ethanesulfonate (esylate), fumarate, gluceptate (glucoheptonate), gluconate, glucuronate, glutamate, hexylresorcinate, hydroxynaphthoate, hippurate, iodide, isethionate, lactate, lactobionate, lauryl sulfate (cstolatc), malatc, maleate, mandelate, mesylate, methanesulfonate, methylnitrate, methylsulfate, mucate, naphthoate, napsylate, nitrate, octadecanoate, oleate, oxalate, pamoate, pantothenate, phosphate, polygalacturonate, salicylate, stearate, succinate, sulfate, sulfosalicylate, tannate, tartrate, teoclate, toluenesulfonate (tosylate), and trifluoroacetate.

8. The compound of claim 1, where $X^-$ is selected from the group consisting of chloride, bromide, iodide, sulfate, methanesulfonate, benzenesulfonate, and toluenesulfonate.

9. The compound of claim 1, wherein the compound is isolated and has an $IC_{50}$ for binding to a muscarinic acetylcholine receptor of less than about 3 nanomolar.

10. A pharmaceutical composition, comprising the stereochemically pure compound of claim 1 with a stereochemical purity of at least 80% and a pharmaceutically acceptable excipient.

11. The pharmaceutical composition of claim 10, wherein in the compound of Formula (II) $R_1$ is unsubstituted phenyl, and $R_2$ is cyclopentyl.

12. The pharmaceutical composition of claim 10, further comprising one or more additional therapeutic agents.

13. The pharmaceutical composition of claim 10, further comprising one or more additional pharmaceutically acceptable excipients.

14. The compound of claim 1, where $X^\ominus$ is bromide.

* * * * *